US011147928B2

(12) United States Patent
Shluzas et al.

(10) Patent No.: US 11,147,928 B2
(45) Date of Patent: *Oct. 19, 2021

(54) SYSTEM AND METHOD FOR DRUG DELIVERY WITH A SAFETY SYRINGE

(71) Applicant: CREDENCE MEDSYSTEMS, INC., Menlo Park, CA (US)

(72) Inventors: Alan E. Shluzas, San Carlos, CA (US); Stephen H. Diaz, Palo Alto, CA (US); John F. Shanley, Emerald Hills, CA (US); Jeff Tillack, Foster City, CA (US); Dan Thayer, Tustin, CA (US)

(73) Assignee: CREDENCE MEDSYSTEMS, INC., Menlo Park, CA (US)

( * ) Notice: Subject to any disclaimer, the term of this patent is extended or adjusted under 35 U.S.C. 154(b) by 71 days.

This patent is subject to a terminal disclaimer.

(21) Appl. No.: 16/420,626

(22) Filed: May 23, 2019

(65) Prior Publication Data
US 2019/0344021 A1    Nov. 14, 2019

Related U.S. Application Data

(63) Continuation of application No. 14/543,787, filed on Nov. 17, 2014, now Pat. No. 10,300,217.
(Continued)

(51) Int. Cl.
*A61M 5/32* (2006.01)
*A61M 5/24* (2006.01)
*A61M 5/315* (2006.01)

(52) U.S. Cl.
CPC ........ *A61M 5/3221* (2013.01); *A61M 5/2466* (2013.01); *A61M 5/322* (2013.01);
(Continued)

(58) Field of Classification Search
CPC ..................... A61M 2005/3231; A61M 5/322
See application file for complete search history.

(56) References Cited

U.S. PATENT DOCUMENTS 2,653,607 A    9/1953  Deans
4,838,870 A    6/1989  Haber et al.
(Continued)

FOREIGN PATENT DOCUMENTS

CN    101318041    12/2008
EP      2022521     2/2009
(Continued)

OTHER PUBLICATIONS

Notice of Allowance for U.S. Appl. No. 16/234,054 dated Oct. 16, 2020.
(Continued)

*Primary Examiner* — Deanna K Hall
(74) *Attorney, Agent, or Firm* — Vista IP Law Group, LLP

(57) ABSTRACT

One embodiment is directed to a system for injecting, comprising a syringe body defining an interior medicine chamber; a stopper member configured to be inserted into the interior medicine chamber to contain medicine within the medicine chamber; a plunger member configured to be manually manipulated to insert the stopper member relative to the syringe body; a needle having proximal and distal ends, the proximal end comprising an anchoring geometry configured to be at least partially penetrated into the stopper member such that upon retraction of the stopper member, the needle is pulled proximally along with the stopper to be at least partially contained within the interior medicine chamber; and an energy-storing member operatively coupled between the stopper member and the syringe body, the
(Continued)

energy-storing member configured to facilitate retraction of the stopper member relative to the syringe body.

20 Claims, 27 Drawing Sheets

Related U.S. Application Data

(60) Provisional application No. 61/904,901, filed on Nov. 15, 2013.

(52) U.S. Cl.
CPC ....... *A61M 5/3234* (2013.01); *A61M 5/31513* (2013.01); *A61M 2005/2474* (2013.01); *A61M 2005/3231* (2013.01); *A61M 2005/3241* (2013.01)

(56) References Cited

U.S. PATENT DOCUMENTS

| | | | |
|---|---|---|---|
| 4,874,381 | A | 10/1989 | Vetter |
| 4,908,022 | A | 3/1990 | Haber |
| 4,927,414 | A | 5/1990 | Kulli |
| 4,944,723 | A | 7/1990 | Haber et al. |
| 4,955,870 | A | 9/1990 | Ridderheim et al. |
| 4,995,870 | A | 2/1991 | Baskas |
| 5,002,536 | A | 3/1991 | Thompson et al. |
| 5,053,010 | A | 10/1991 | McGary et al. |
| 5,112,316 | A | 5/1992 | Venturini |
| 5,211,628 | A | 5/1993 | Marshall |
| 5,215,533 | A | 6/1993 | Robb |
| 5,330,430 | A | 7/1994 | Sullivan |
| 5,342,310 | A | 8/1994 | Ueyama et al. |
| 5,343,310 | A | 8/1994 | Ueyama et al. |
| 5,403,288 | A | 4/1995 | Stanners |
| 5,615,772 | A | 4/1997 | Naganuma |
| 5,669,887 | A | 9/1997 | Cooper |
| 5,676,346 | A | 10/1997 | Leinsing |
| 5,681,292 | A | 10/1997 | Tober et al. |
| 5,704,918 | A | 1/1998 | Higashikawa |
| 5,782,804 | A | 7/1998 | McMahon |
| 5,792,107 | A | 8/1998 | Petrocelli |
| 5,971,964 | A | 10/1999 | Donaldson |
| 5,993,418 | A | 11/1999 | Alexander |
| 6,010,486 | A | 1/2000 | Carter et al. |
| 6,090,081 | A | 7/2000 | Sudo et al. |
| 6,183,440 | B1 | 2/2001 | Bell |
| 6,413,237 | B1 | 7/2002 | Caizza et al. |
| 6,585,700 | B1 | 7/2003 | Trocki et al. |
| 6,709,019 | B2 | 3/2004 | Parker et al. |
| 7,500,964 | B2 | 3/2009 | Shaw et al. |
| 8,088,104 | B2 | 1/2012 | Smith et al. |
| 8,167,837 | B2 | 5/2012 | Judd et al. |
| 9,919,110 | B2 | 3/2018 | Diaz et al. |
| 1,001,067 | A1 | 7/2018 | Shluzas et al. |
| 10,300,217 | B2 * | 5/2019 | Shluzas ............... A61M 5/3221 |
| 2003/0004468 | A1 | 1/2003 | Righi et al. |
| 2004/0215150 | A1 | 10/2004 | Shue et al. |
| 2006/0253074 | A1 | 11/2006 | Thayer |
| 2006/0258984 | A1 | 11/2006 | Kiehne |
| 2007/0129675 | A1 | 6/2007 | Summerville et al. |
| 2008/0027381 | A1 | 1/2008 | Smith et al. |
| 2008/0269690 | A1 | 10/2008 | Felix-Faure |
| 2009/0018503 | A1 | 1/2009 | Walton et al. |
| 2009/0259195 | A1 | 10/2009 | Lin Lee |
| 2010/0010450 | A1 | 1/2010 | Runfola et al. |
| 2010/0256560 | A1 | 10/2010 | Li |
| 2010/0262119 | A1 | 10/2010 | Schraga |
| 2010/0286609 | A1 | 11/2010 | Mahurkar |
| 2013/0030382 | A1 | 1/2013 | Sudo |
| 2013/0035664 | A1 | 2/2013 | Mojdehbakhsh et al. |
| 2013/0060191 | A1 | 3/2013 | Thorley et al. |
| 2013/0079716 | A1 | 3/2013 | Thorley et al. |
| 2015/0073344 | A1 | 3/2015 | Van Damme et al. |
| 2018/0296770 | A1 | 10/2018 | Diaz et al. |

FOREIGN PATENT DOCUMENTS

| | | |
|---|---|---|
| JP | 05500621 | 2/1993 |
| JP | 2004-321775 | 11/2004 |
| JP | 2006-520219 | 9/2006 |
| JP | 2007514486 | 6/2007 |
| JP | 2008535589 | 9/2008 |
| JP | 2009540875 | 11/2009 |
| JP | 2009-543616 | 12/2009 |
| JP | 2011509810 | 3/2011 |
| JP | 2012519511 | 8/2012 |
| KR | 20130000843 | 2/2013 |
| WO | WO 90/06146 | 6/1990 |
| WO | WO 91/04065 | 4/1991 |
| WO | WO 93/18808 | 9/1993 |
| WO | WO 2003/039634 | 5/2003 |
| WO | WO 2004/082747 | 9/2004 |
| WO | WO 2005058398 | 6/2005 |
| WO | WO 2005058399 | 6/2005 |
| WO | WO 2006/108243 | 10/2006 |
| WO | WO 2007/130388 | 11/2007 |
| WO | WO 2008/009063 | 1/2008 |
| WO | WO 2009/094345 | 11/2009 |
| WO | WO 2010065375 | 6/2010 |
| WO | WO 2010/100241 | 9/2010 |
| WO | WO 2010/100243 | 9/2010 |
| WO | WO 2010/100244 | 9/2010 |
| WO | WO 2011/075760 | 6/2011 |
| WO | WO 2012038959 | 3/2012 |
| WO | WO 2012/073035 | 6/2012 |
| WO | WO 2012151314 | 8/2012 |
| WO | WO 2015/003016 | 1/2015 |
| WO | WO 2015/164839 | 10/2015 |

OTHER PUBLICATIONS

Notice of Allowance for U.S. Appl. No. 14/321,706 dated Aug. 24, 2017.
Amendment and Response to Non-Final Office Action for U.S. Appl. No. 14/321,713 dated Oct. 13, 2017.
Notice of Allowance for U.S. Appl. No. 14/321,713 dated Nov. 8, 2017.
Amendment and Response to Final Office Action for U.S. Appl. No. 14/696,342 dated Nov. 6, 2017.
Notice of Allowance for U.S. Appl. No. 14/321,735 dated Aug. 31, 2017.
Amendment Response to Final Office Action for U.S. Appl. No. 14/543,787 dated Sep. 11, 2017.
Notice of Allowance for U.S. Appl. No. 14/321,721 dated Sep. 22, 2017.
Notice of Allowance for U.S. Appl. No. 14/321,729 dated Sep. 22, 2017.
Non-Final Office Action for U.S. Appl. No. 14/956,282 dated Dec. 27, 2017.
Notice of Allowance dated Dec. 12, 2017 for U.S. Appl. No. 14/696,342.
Non-Final Office Action for U.S. Appl. No. 14/543,787 dated Nov. 27, 2017.
Extended European Search Report dated Jun. 23, 2017 for EP Application No. 14862453.9, Credence Medsystems, Inc.
Response to Extended European Search Report and Rule 70(2) filed Sep. 20, 2017 for EP application No. 14819246.1, Credence Medsystems Inc.
Response to Extended European Search Report and Rule 70(2) filed Jan. 19, 2018 for EP application No. 14862453.9, Credence Medsystems Inc.
First Examination Report dated Feb. 21, 2018 for Australian application No. 2014284373, Credence MedSystems Inc.
Extended European Search Report dated Feb. 5, 2018 for EP Application No. 15782398.0, Credence Medsystems, Inc.

(56) References Cited

OTHER PUBLICATIONS

Voluntary Amendments filed Jan. 6, 2017 for EP application No. 14862453.9, Credence MedSystems Inc.
Amendment and Response to Office Action for U.S. Appl. No. 14/956,282, dated Mar. 27, 2018.
Final Office Action for U.S. Appl. No. 14/956,282 dated May 4, 2018.
Notice of Allowance and Issue Fee due for U.S. Appl. No. 14/696,342 dated Apr. 20, 2018.
Amendment and Response to Non-Final Office Action for U.S. Appl. No. 14/543,787 filed Feb. 27, 2018.
Final Office Action for U.S. Appl. No. 14/543,787 dated Apr. 9, 2018.
Official Action for Japanese Application No. 2016-524332 dated Mar. 2, 2018.
Amendment and Response filed Jun. 4, 2018 for Japanese Patent Application No. 2016-524332 (23 pages).
First Examination Report dated Jun. 4, 2018 for Chinese application No. 2014800480204, Credence MedSystems Inc.
First Examination Report dated Jul. 25, 2018 for Australian application No. 2014348292, Credence Medsystems Inc.
Notice of Appeal and Pre-Appeal Brief filed Jul. 9, 2018 for U.S. Appl. No. 14/543,787.
Notice of Allowance and Fee(s) Due dated Aug. 30, 2018 for U.S. Appl. No. 14/956,282.
Official Action dated Sep. 12, 2018 for Japanese Patent Application No. 2016-531649, Credence Medsystems Inc.
Examination Response to an Examiner's Report dated Oct. 10, 2018 for Australian application No. 2014284373, Credence Medsystems Inc.
Notice of Acceptance dated Oct. 24, 2018 for Australian Patent Application No. 2014284373, Credence Medsystems Inc.
Notice of Allowance and Fee(s) Due dated Oct. 31, 2018 for U.S. Appl. No. 14/543,787, filed Nov. 17, 2014.
Notice of Allowance dated Nov. 2, 2018 for Japanese Patent Application No. 2016-524332, Credence Medsystems Inc.
Response to European search report dated Aug. 28, 2018 for European Patent Application No. 15782398, Credence Medsystems Inc.
Response to First Office Action dated Oct. 18, 2018 for Chinese Patent Application No. 201480048020.4, Credence Medsystems Inc.
Response to Office Action dated Jan. 7, 2019 for Japanese Patent Application No. 2016-531649, Credence Medsystems Inc.
Response to First Examination Report dated Feb. 20, 2019 for Australian Patent Application No. 2014348292, Credence Medsystems Inc.
Communication under Rule 71(3) EPC dated Mar. 14, 2019 for European Patent Application No. 14862453, Credence Medsystems Inc.
Second Examination Report dated Feb. 25, 2019 for Australian Patent Application No. 2014348292, Credence Medsystems Inc.
Second Examination Report dated Feb. 26, 2019 for Chinese Patent Application No. 201480048020.4, Credence Medsystems Inc.
Response to First Office Action dated Mar. 18, 2019 for Chinese Patent Application No. 201480073161.1, Credence Medsystems Inc.
Official Action dated Feb. 13, 2019 for Japanese Patent Application No. 2016-564243, Credence Medsystems Inc.
Notice of Allowance dated Jan. 15, 2019 for U.S. Appl. No. 14/543,787.
Notice of Allowance dated Feb. 28, 2019 for U.S. Appl. No. 15/921,262.
Amendment Response to Non-Final Office Action for U.S. Appl. No. 14/321,706 dated Jul. 28, 2017.
International Search Report and Written Opinion dated Nov. 19, 2015, International Patent Application No. PCT/US15/027670 with International Filing Date of Apr. 24, 2014, (18 pages).
Non-Final Office Action for U.S. Appl. No. 14/696,342 dated Apr. 14, 2017.
Amendment Response to Non-Final Office Action for U.S. Appl. No. 14/696,342, dated Jul. 14, 2017.
Amendment Response to Non-Final Office Action for U.S. Appl. No. 14/543,787, dated Feb. 28, 2017.
Amendment Response to Non-Final Office Action for U.S. Appl. No. 14/321,735 dated Aug. 2, 2017.
Final Office Action for U.S. Appl. No. 14/696,342 dated Aug. 4, 2017.
Amendment Response to Non-Final Office Action for U.S. Appl. No. 14/321,721 dated Aug. 25, 2017.
Amendment Response to Non-Final Office Action for U.S. Appl. No. 14/321,729 dated Aug. 25, 2017.
Foreign Submission Reply for EP Patent Appln. No. 14819246.1 dated Sep. 29, 2020.
Official Action dated Apr. 2, 2019 for Japanese Patent Application No. 2018-106846.
Response to Second Office Action filed May 7, 2019 for Chinese Patent Application No. 201480048020.4.
Response to Official Action dated May 10, 2019 for Japanese Patent Application No. 2016-564243, Credence Medsystems Inc.
Response to Second Examination Report dated Apr. 30, 2019 for Australian Patent Application No. 2014348292.
Notice of Acceptance for patent application dated May 13, 2019 for Australian Patent Application No. 2014348292.
Non-Final Office Action for U.S. Appl. No. 16/234,054 dated Jun. 29, 2020.
Amendment Response to Non-Final Office Action for U.S. Appl. No. 16/234,054 dated Sep. 28, 2020.
Foreign OA for JP Patent Appln. No. 2019-131622 dated Mar. 23, 2021.
Non-Final Office Action for U.S. Appl. No. 16/502,372 dated Jan. 14, 2021.
Foreign NOA for IL Patent Appln. No. 243339 dated Mar. 10, 2021.
Foreign Response for IL Patent Appln. No. 243339 dated Jan. 3, 2021.
Final Office Action for U.S. Appl. No. 16/502,372 dated May 11, 2021.
Notice of Allowance for U.S. Appl. No. 16/502,372 dated Jul. 26, 2021.
Extended European Search Report for EP Patent Appln. No. 21166720.9 dated Jun. 4, 2021.
Foreign Exam Report for IN Patent Appln. No. 201647040151 dated May 24, 2021.
Foreign Exam Report for CA Patent Appln. No. 2980443 dated May 25, 2021.
Foreign OA for JP Patent Appln. No. 2020-161777 dated Jul. 20, 2021.

* cited by examiner

SECTION B-B

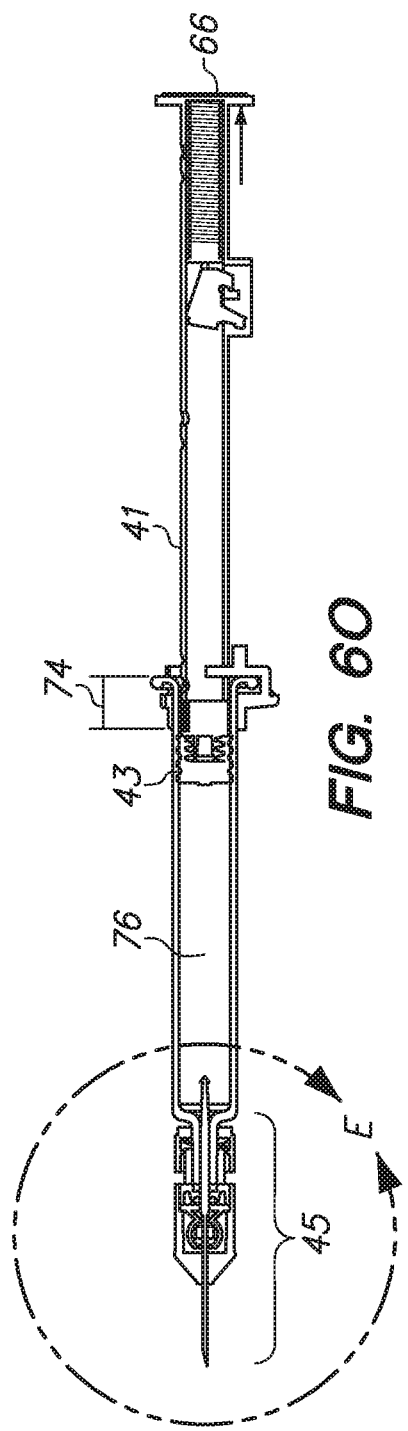
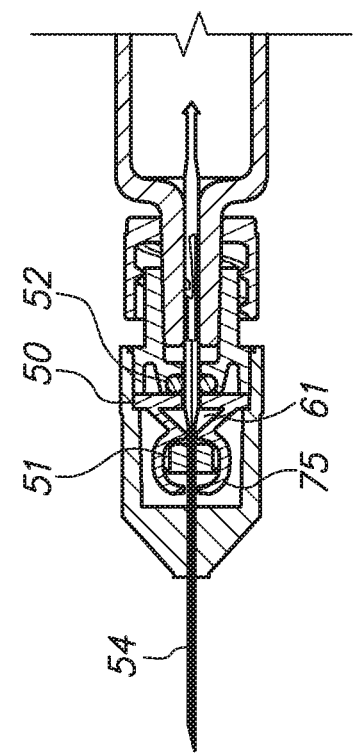
FIG. 6O
FIG. 6P

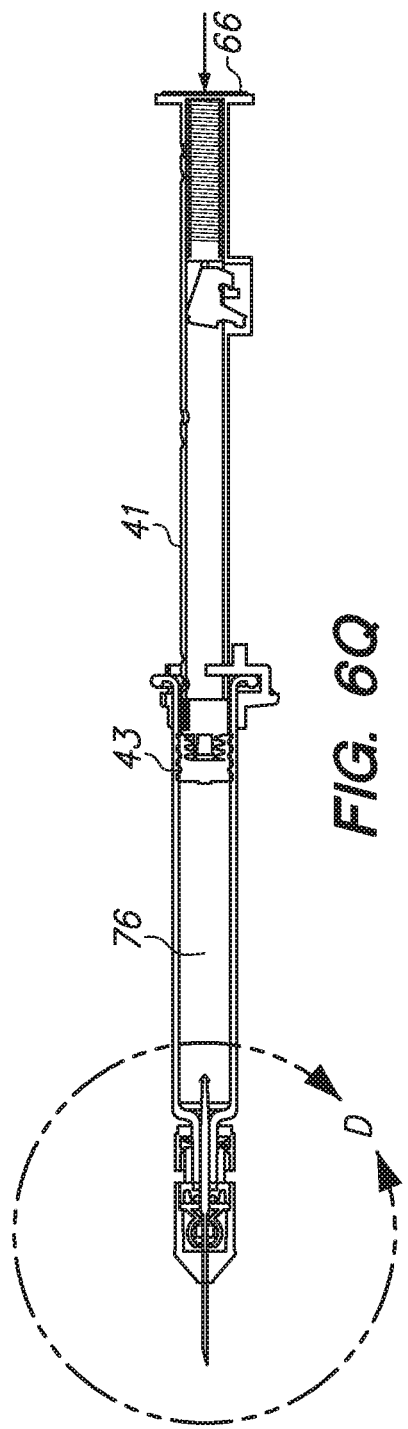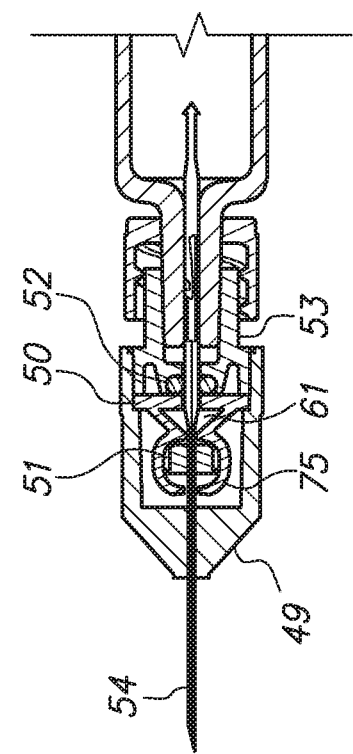

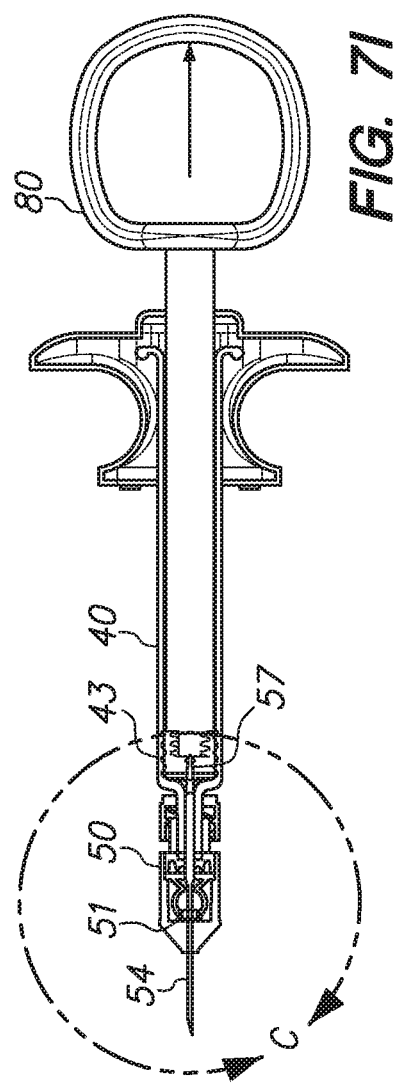
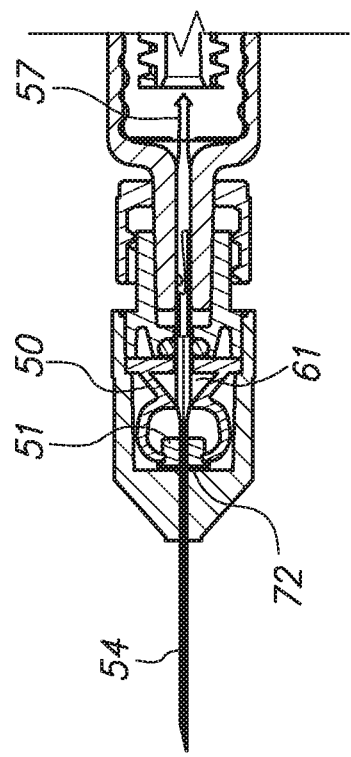
FIG. 7I
FIG. 7J

SYSTEM AND METHOD FOR DRUG DELIVERY WITH A SAFETY SYRINGE

RELATED APPLICATION DATA

The present application is a continuation of U.S. patent application Ser. No. 14/543,787 filed Nov. 17, 2014, which claims the benefit under 35 U.S.C. § 119 to U.S. provisional patent application Ser. No. 61/904,901 filed Nov. 15, 2013. The foregoing applications are hereby incorporated by reference into the present application in their entirety.

FIELD OF THE INVENTION

The present invention relates generally to injection systems, devices, and processes for facilitating various levels of control over fluid infusion, and more particularly to systems and methods related to safety syringes in an environment wherein it is desired to have the sharp point of the needle be retracted after the injection is completed.

BACKGROUND

Millions of syringes, such as that depicted in FIG. 1 (2), are consumed in healthcare environments every day. A typical syringe (2) comprises a tubular body (4), a plunger (6), and an injection needle (8). Typical syringes are supplied empty and may be filled from a medicine vial at the point of use. FIG. 2 illustrates the process of filling a syringe (2) with a needle (8) from a vial of liquid injectable medicine (10). The medicine can be liquid or a powder mixed with a liquid at the time of use. FIG. 3 shows the needle (8) which is used with traditional syringes (12). The needle is connected to the syringe with a needle hub (19), and a luer lock adapter (14) on the front of the syringe.

The use of needle injection configurations, carries with it the risk of a sharp needle contacting or poking a structure that is not desired. For this reason, so called "safety syringes" have been developed. One safety syringe (20) configuration is shown in FIG. 4, wherein a tubular shield member (22) is spring biased to cover the needle (8) when released from a locked position relative to the syringe body (4).

Such a configuration may be perceived suboptimally by users as bulky and cumbersome to use. For example, the external spring based shield is relatively large, and may rapidly activate, thereby spraying blood particles in unwanted directions, such as on the user. In some instances it is desirable to pre-fill the syringe with drug at the factory to eliminate the filling step shown in FIG. 2. Further, existing safety syringe configurations generally are not compatible with being pre-filled with drug. Common drugs for injection may be in liquid form, or may comprise a powder mixed with a liquid at the time of use. The elastomer and polymer materials of such a system can leech materials, moisture, or oxygen into liquid contained within the syringe body over time. Pre-filled glass syringe bodies are shown in FIG. 5. The pre-filled syringe is constructed of a glass tubular body (4) with a plunger (6) attached to a stopper (5) and either a permanently coupled needle (8) or a luer lock connection (14) for connection of a needle at the point of use. The glass body is used to minimize any leeching of contaminants, moisture, or oxygen into the drug. These glass syringe bodies generally are not compatible with current safety syringe systems. There is a need for improved injection systems which address the shortcomings of currently-available configurations.

BRIEF DESCRIPTION OF THE DRAWINGS

FIGS. 7A-7L illustrate various aspects of one embodiment of an adaptable safety syringe assembly in accordance with the present invention, wherein the needle is manually retracted upon giving an injection.

SUMMARY OF THE INVENTION

Figure 1:
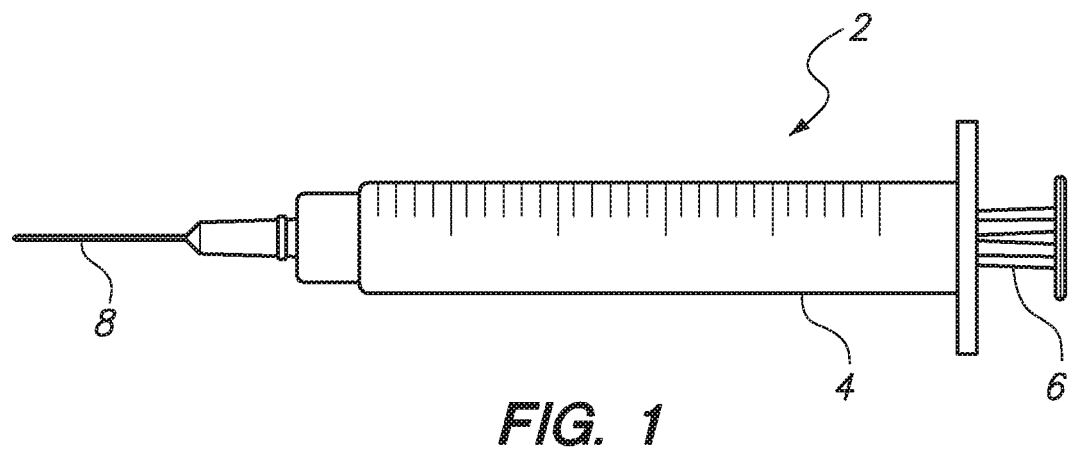
FIGS. 1-5 illustrate various aspects of conventional injection syringe configurations.
Figure 2:
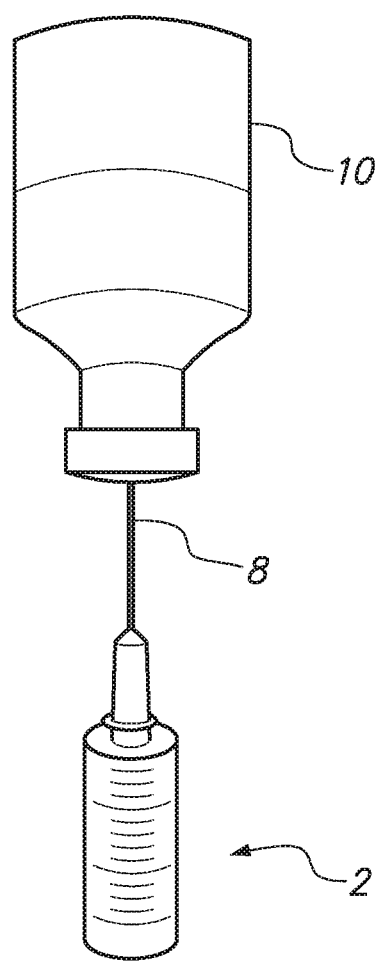
Figure 3:
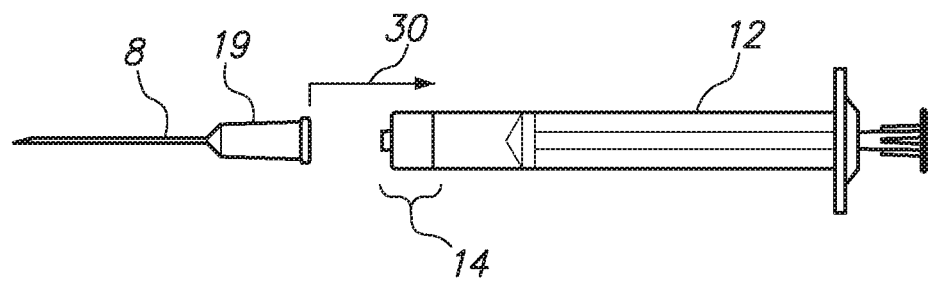
Figure 4:
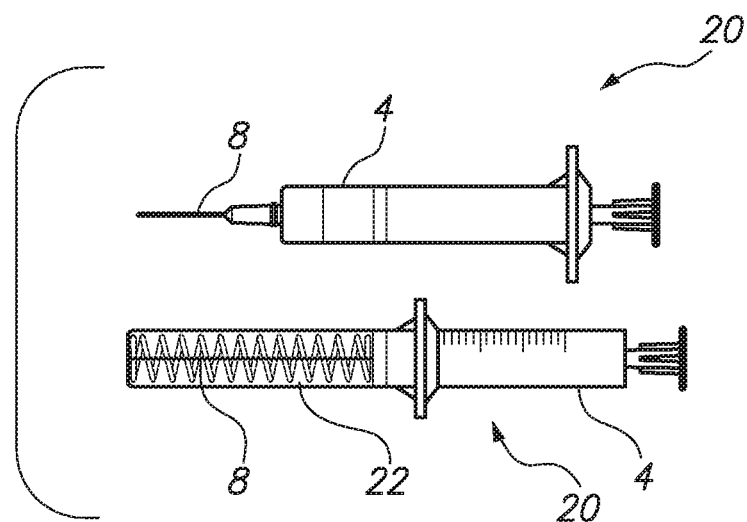
Figure 5:
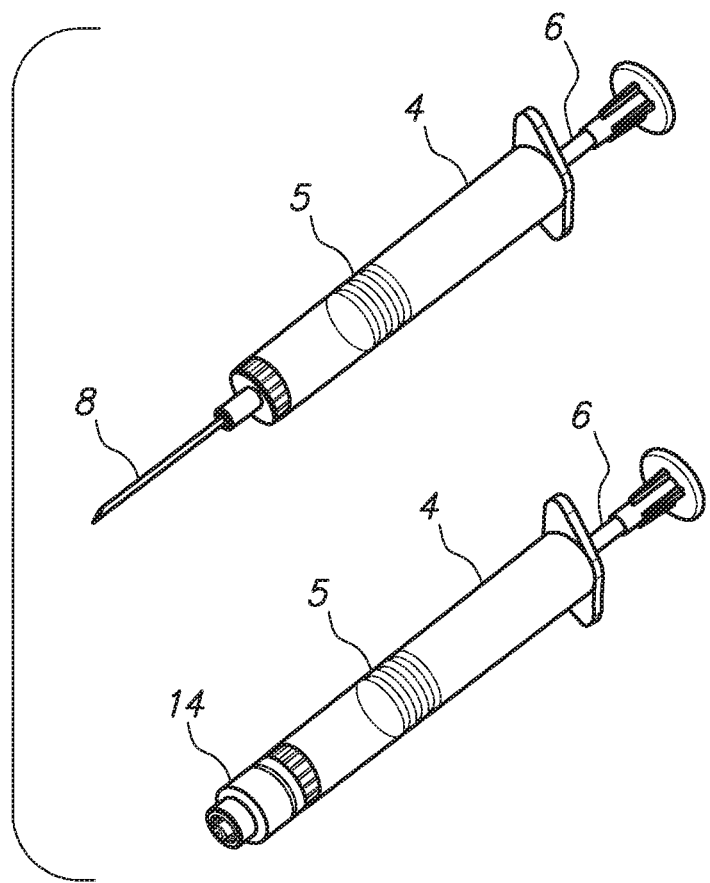

One embodiment is directed to a method of conducting an injection, comprising: providing an assembly of a syringe plunger coupled to a syringe stopper, inside a syringe body which may contain fluid for infusion. A syringe body having a distal end that is coupled to a needle assembly and a proximal end which may be coupled to a handle. A syringe plunger may be configured to move the syringe stopper in the syringe body to expel the fluid for infusion out of the needle. A needle assembly may be constructed of a needle and a needle housing. A needle may be constructed of a cannula, a cannula hub, and a barb. The needle may be configured to be held in place by the needle housing during the injection process. At or near the completion of the injection, the needle may be configured to attach to the syringe stopper, and the needle housing may be configured to release the needle, so the needle may be retracted into the syringe body. The syringe plunger may be constructed of a plunger body, plunger tip, latch, and retraction element. The syringe plunger body may be configured to cooperate with a latch component hold a retraction element which may be configured to retract the needle upon completion of the injection. Upon retraction into the syringe body, the needle housing may be configured to block the hole so the needle cannot be re-exposed out of the syringe body or needle housing.

Another embodiment is directed to a method of conducting an injection, comprising: providing an assembly of a syringe plunger coupled to a syringe stopper, inside a syringe body which may contain fluid for infusion. The syringe body having a distal end that may be coupled to a needle assembly and a proximal end which may be coupled to a handle. The syringe plunger may be configured to move the syringe stopper in the syringe body to expel the fluid for infusion out of the needle. The needle assembly may be constructed of a needle and a needle housing. The needle may be constructed of a cannula, a cannula hub, and a barb. The needle may be configured to be held in place by the needle housing during the injection process. At or near the completion of the injection, the needle may be configured to couple to the syringe stopper, and the needle housing may be configured to release the needle, so the needle can be retracted into the syringe body. The syringe plunger may be configured to allow for manual retraction of the needle inside the syringe body. Upon retraction into the syringe body, the needle housing may be configured to block the hole so the needle cannot be re-extended out of the syringe body or needle housing.

Another embodiment is directed to a method of conducting an injection, comprising: providing an assembly of a syringe plunger coupled to a syringe stopper, inside a syringe body which may contain fluid for infusion. The syringe body having a distal end that may be coupled to a needle assembly and a proximal end which may be coupled to a handle. The syringe plunger may be configured to move the syringe stopper in the syringe body to expel the fluid for infusion out of the needle. The needle assembly may be constructed of a needle and a needle housing. The needle may be constructed of a cannula, a cannula hub, and a barb. The needle may be configured to be held in place by the needle housing during the injection process. At or near the completion of the injection, the needle may be configured to couple to the syringe stopper, and the needle housing may be configured to release the needle, so the needle can be retracted into the syringe body. The syringe plunger may comprise a plunger stem, plunger tip, thumb pad, rear base, brake retainer, brake, and retraction element. The syringe plunger may be configured to store energy by loading a retraction element during antegrade motion of the plunger during the injection stroke. Retrograde motion of the syringe plunger may be restrained by a brake component during the injection process. The brake component may be configured to release the plunger upon completion of the injection allowing the stored energy to be released causing retrograde motion of the plunger and coupled needle to retract the needle into the syringe body. Upon retraction into the syringe body, the needle housing may be configured to block the hole so the needle cannot be re-extended out of the syringe body or needle housing.

Another embodiment is directed to a system for injecting, comprising a syringe body defining an interior medicine chamber; a stopper member configured to be inserted into the interior medicine chamber to contain medicine within the medicine chamber; a plunger member configured to be manually manipulated to insert the stopper member relative to the syringe body; a needle having proximal and distal ends, the proximal end comprising an anchoring geometry configured to be at least partially penetrated into the stopper member such that upon retraction of the stopper member, the needle is pulled proximally along with the stopper to be at least partially contained within the interior medicine chamber; and an energy-storing member operatively coupled between the stopper member and the syringe body, the energy-storing member configured to facilitate retraction of the stopper member relative to the syringe body. The plunger member may comprise a plunger member body that defines an interior volume, and wherein the energy-storing member is housed substantially inside of the plunger member body interior volume. The system further may comprise a latch member operatively coupled to the plunger member and housed substantially within the plunger member body interior volume, the latch member being configured to have a first mechanical state wherein the latch member maintains the energy storing member in an energy-storing state, and a second mechanical state wherein the latch member allows the energy-storing member to release energy stored by the energy-storing member to assist in retraction of the stopper member relative to the syringe body. The latch member may comprise a triggering portion configured to extend outside of the plunger member body interior volume and operatively couple to the syringe body such that the energy-storing member may be automatically released when the plunger member and intercoupled stopper member reach a predetermined insertional position relative to the syringe body. The predetermined insertional position may be one wherein the stopper is positioned in a full insertion state relative to the syringe body. The energy-storing member may be a spring. The spring may comprise a material selected from the group consisting of: stainless steel, carbon steel, beryllium copper alloy, nickel-titanium alloy, chrome-silicon alloy, and cobalt-nickel alloy. The spring may comprise an elastomeric polymer. The elastomeric polymer may be selected from the group consisting of: a styrenic polymer, a co-polyester polymer, polyurethane, polyamide, a polyolefin blend, a polyolefin alloy, a polyolefin plastomer, a polyolefin plastomer, and rubber. The energy-storing member may comprise a solid pellet member. The solid pellet member may be an elastomeric polymer selected from the group consisting of: a styrenic polymer, a co-polyester polymer, polyurethane, polyamide, a polyolefin blend, a polyolefin alloy, a polyolefin plastomer, a polyolefin plastomer, and rubber. The spring may comprise a single generally helically-shaped coil. The spring may comprise a plurality of generally helically-shaped coils. At least two of the coils comprising the plurality of generally helically-shaped coils may be co-axially aligned. At least two of the coils comprising the plurality of generally helically-shaped coils may be longitudinally parallel aligned. The co-axially aligned helically-shaped coils may be also longitudinally parallel aligned. The co-axially and longitudinally parallel aligned helically-shaped coils may be helically wound with opposite winding directions relative to each other to prevent coil interference upon compression of the coils. Retraction of the plunger may retract the intercoupled stopper member and needle, such that at least a portion of the needle is withdrawn into the interior medicine chamber of the syringe body. The plunger member may have a threaded tip, and a hollow recess. The plunger tip hollow recess may be configured to allow the needle proximal end to fully penetrate the stopper. The syringe body may comprise glass. The syringe body may comprise a polymer. The stopper member may comprise butyl rubber. The latch may comprise a polymer selected from the group consisting of: polyetherimide, peek, and polyamide. The plunger may comprise a polymer selected from the group consisting of: polyetherimide, peek, and polyamide.

Another embodiment is directed to a system for injecting, comprising a syringe body defining an interior medicine chamber; a stopper member configured to be inserted into the interior medicine chamber to contain medicine within the medicine chamber; a plunger member configured to be manually manipulated to insert the stopper member relative to the syringe body; and a needle having proximal and distal ends, the proximal end comprising an anchoring geometry configured to be at least partially inserted into the stopper member such that upon retraction of the stopper member, the needle is pulled proximally along with the stopper to be at least partially contained within the interior medicine chamber; wherein the stopper member is configured to be at least partially pierced by a sharpened proximal end of the needle, and wherein the needle has at least one anchoring element configured to resist pullout subsequent to being at least partially pierced into the stopper member. The at least one anchoring element may be formed from a piece of sheet stock material. The at least one anchoring element may be selected from the group consisting of: a barb, a skive cut, hook geometry, and an arrowhead geometry. The stopper may have an outer geometry selected to substantially match an inner geometry of the syringe body to substantially seal with the syringe body. The stopper may comprise an elastomeric material selected from the group consisting of: chlorobutyl rubber, bromobutyl rubber, and silicon rubber. The system further may comprise a sealant coating applied to at least a portion of the stopper to isolate medicine materials from the stopper. The sealant coating may comprise a PTFE film. The system further may comprise a lubricant layer introduced between the stopper and the syringe body. The lubricant layer may comprise a silicon oil. A distal portion of the stopper member may comprise a conventional off-the-shelf compliant stopper. The stopper member may comprise an unmodified solid compliant member with no recesses or projections for coupling to a needle. The plunger member may have a threaded tip, and a hollow recess. The plunger tip hollow recess may be configured to allow the needle proximal end to fully penetrate the stopper. The syringe body may comprise glass. The syringe body may comprise a polymer. The sheet stock material may comprise a metal selected from the group consisting of: stainless steel, cobalt-chrome alloy, and titanium. The needle may define a drug passageway therethrough having a proximal entrance which is located distal to a distal end of the stopper member when the sharpened proximal end of the needle is penetrated into the stopper member.

DETAILED DESCRIPTION

Figure 6A:
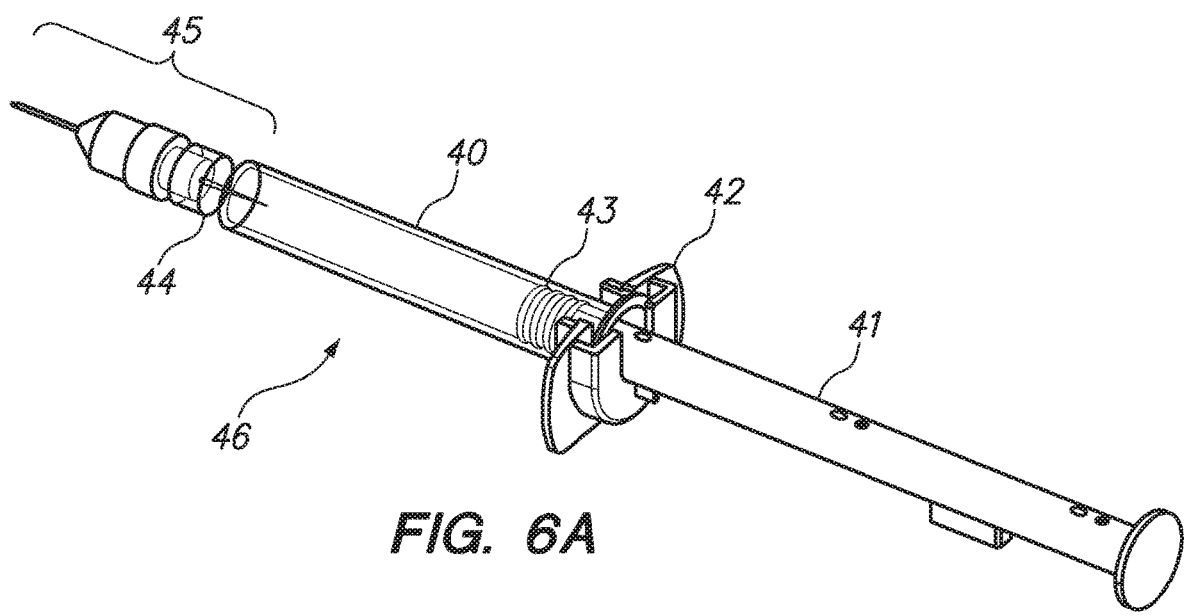
FIGS. 6A-6V illustrate various aspects of one embodiment of a safety syringe assembly in accordance with the present invention, wherein the needle is automatically retracted upon giving an injection.
Figure 6B:
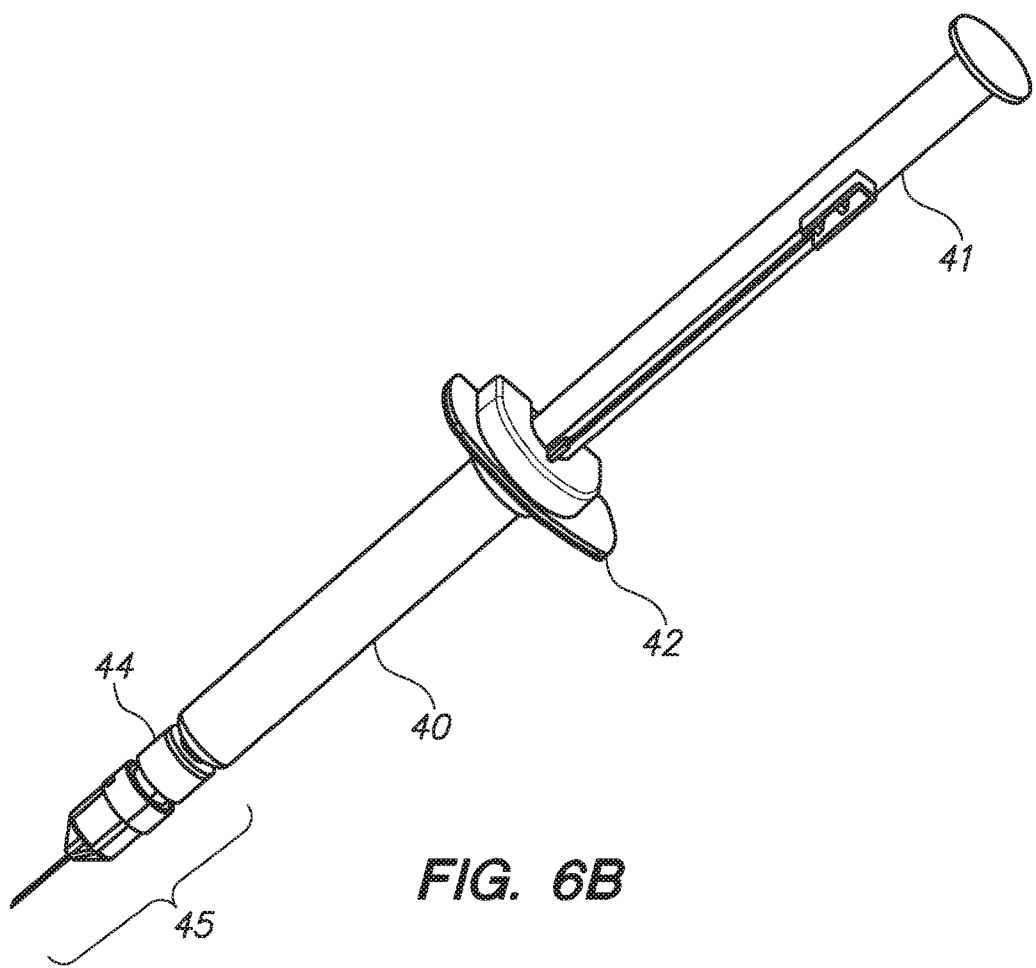
Figure 6C:
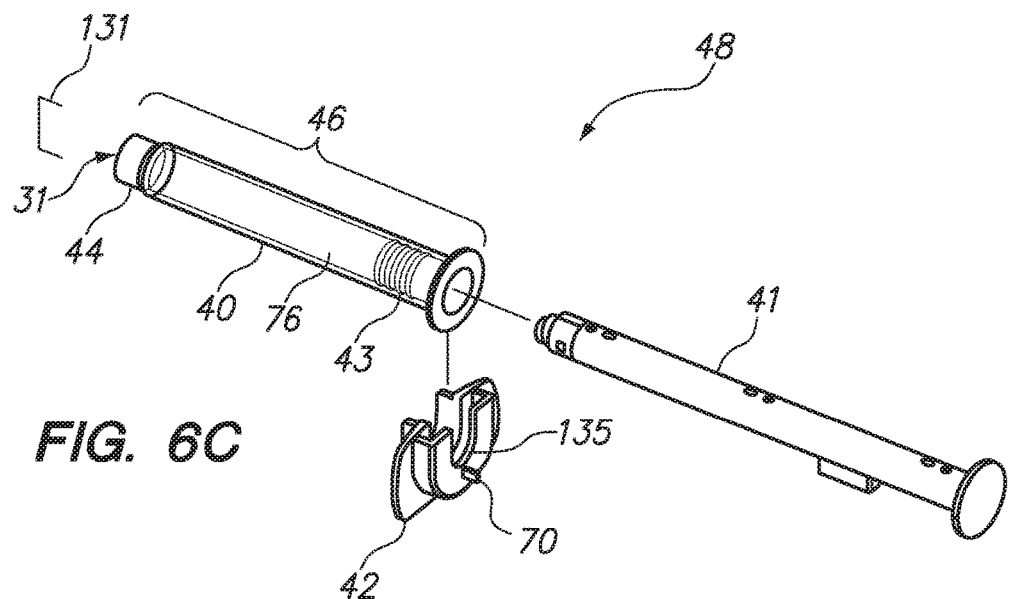
Figure 6D:
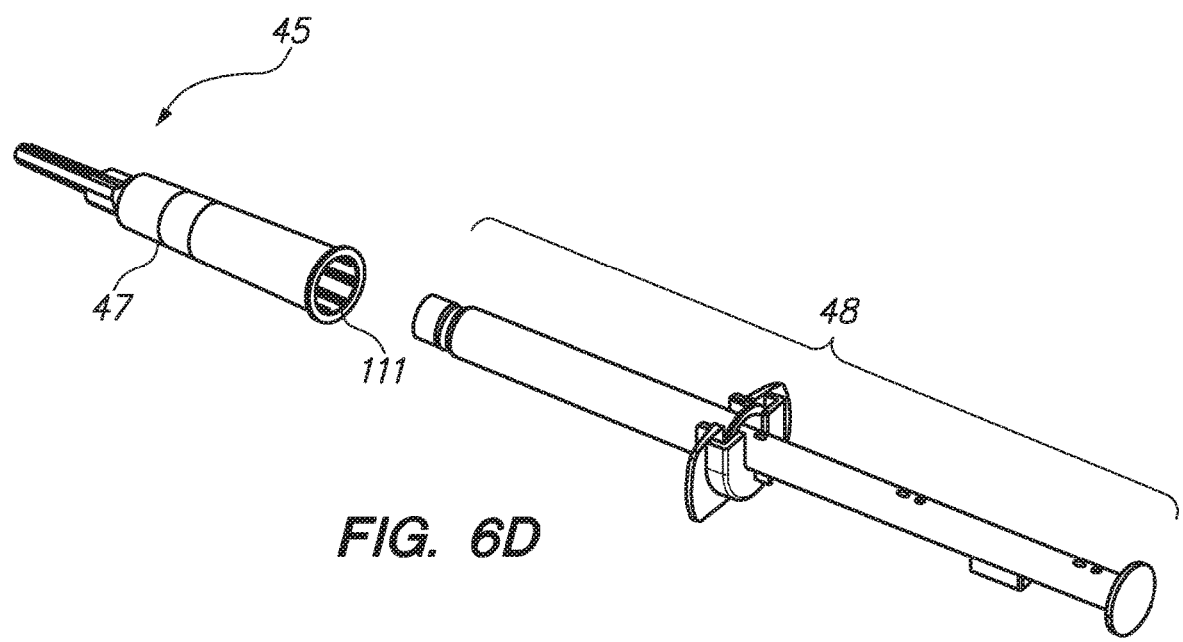
Figure 6E:
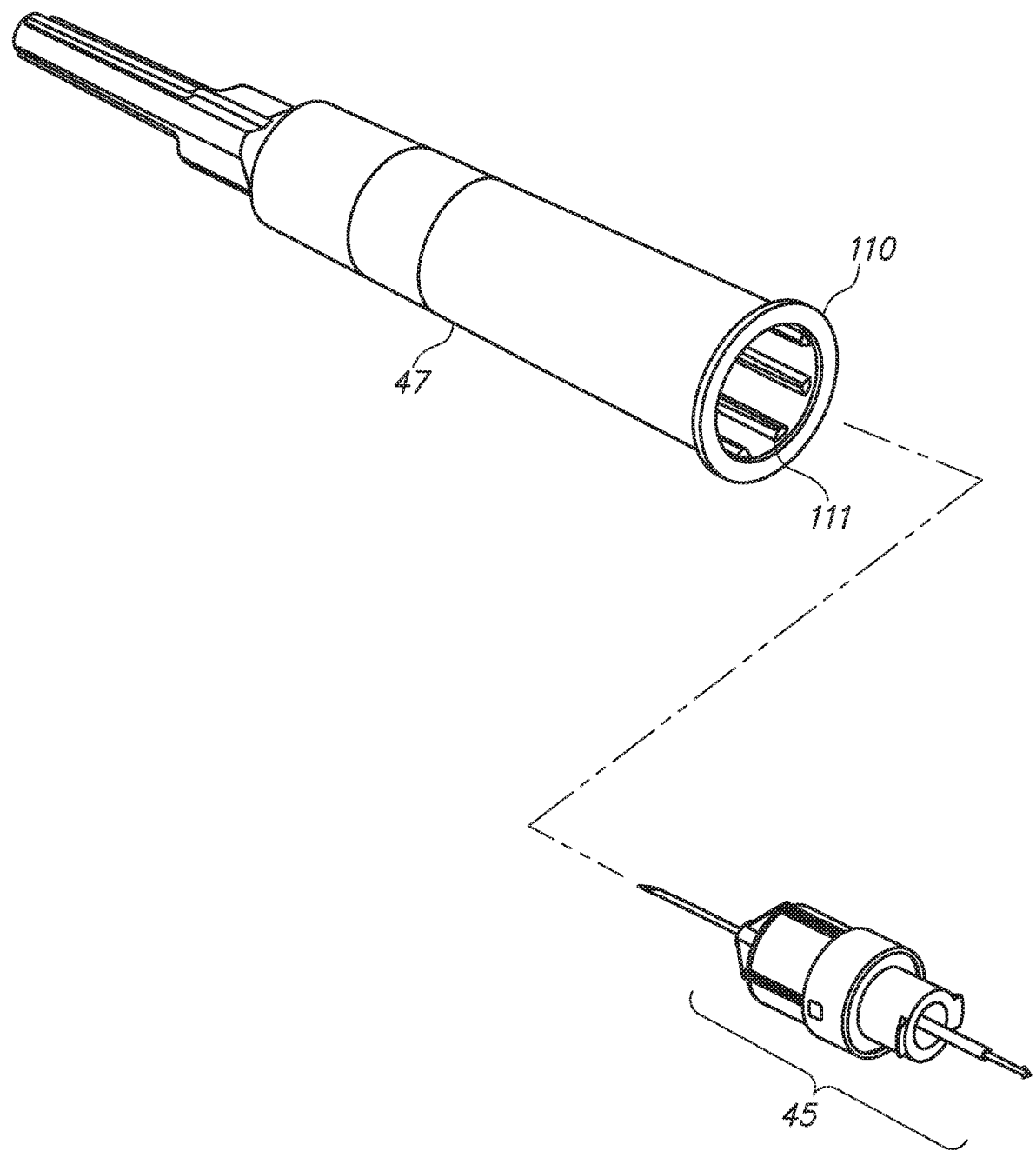

Referring to FIGS. 6A-6D, a safety syringe embodiment is depicted wherein a syringe body is assembled into a full safety syringe by adding a plunger assembly, a handle, and a needle assembly. Referring to FIG. 6A, a syringe body (46) comprising a cylinder (40), a luer lock adapter (44); it may be operatively coupled to a syringe stopper, or stopper member, (43) and is shown operatively coupled to a plunger member (41) inserted therein which engages the stopper member (43). The stopper member (43) may comprise an elastomeric material, such as butyl rubber, chlorobutyl rubber, bromobutyl rubber, and/or silicone rubber. A sealant coating may be applied to at least a portion of the stopper member (43) to isolate medicine materials from the stopper member. The sealant coating may, for example, comprise a PTFE film. A lubricant layer may be introduced between the stopper and the syringe body. The lubricant layer may comprise a silicon oil. A distal portion of the stopper member may comprise a conventional off-the-shelf compliant stopper. The stopper member may comprise an unmodified solid compliant member with no recesses or projections for coupling to a needle. A handle (42) may be coupled to the proximal end of the cylinder (40). The distal portion of the depicted syringe body (46) is of the form of a luer lock adapter (44) which may be selectively coupled to a needle assembly (45). FIG. 6B shows a second isometric view of the items mentioned in FIG. 6A. FIG. 6C is an illustration of the syringe and plunger assembly (48) which may comprise a syringe body (46) a handle (42) and a plunger assembly (41). The syringe and plunger assembly (48) preferably is assembled by the manufacturer, but also may be assembled by the user at the point of care. The syringe body (46) may comprise a cylinder (40), a luer lock adapter (44), and be configured to interface with a stopper member (43), which may be coupled to a plunger member (41), as noted above. The cylinder (40) and stopper member (43) define an interior medicine chamber. In the pre-filled case, drug (76) may be housed inside the cylinder (40) and contained by the stopper (43). The depicted luer lock adapter has a hole (31) disposed therethrough defining an inside diameter for the passage of drug (76) out of the cylinder. A cap (131) may be placed on the tip of the syringe body for shipment, to be removed prior to use. The syringe body may comprise materials such as those selected from the group consisting of: glass, polymers such as COC, COP, nylon, polypropylene, polyethylene, or metals. The syringe stopper preferably comprises a low leachable butyl rubber. However the stopper also or alternatively comprise materials such as silicone rubber, or other elastomeric material. The stopper can be coated with pharmaceutical grade lubricants such as silicon oil, PTFE, or other medical grade lubricants. The stopper can also be covered in a film to provide lubrication and or a drug contaminant barrier. Coupled to the depicted syringe stopper is a syringe plunger (41). The syringe stopper to plunger connection may comprise, for example, a screw connection, press fit, adhesive connection, and/or welded connection. The handle (42) comprises a latch contact surface (70) and an alignment feature (135). The alignment feature cooperates with a slot in the plunger (120 FIG. 6L) to align the two components. The alignment feature (135) also prevents the plunger from being withdrawn from the syringe body (46) when the handle (42) is installed. FIG. 6D illustrates a completed syringe and plunger assembly (48) with a needle assembly (45) disposed within a needle cover (47). The needle cover may be configured with ribs (111) to align the barb end of the needle with the ID of the tip of the luer lock adapter (44) during installation by the user. Alternate alignment geometries such as bumps, multiple annular rings, or flexible structures could also be used for alignment. Alternatively, the needle (45) may be pre-coupled to the syringe and plunger assembly (48) by the manufacturer.

Figure 6F:
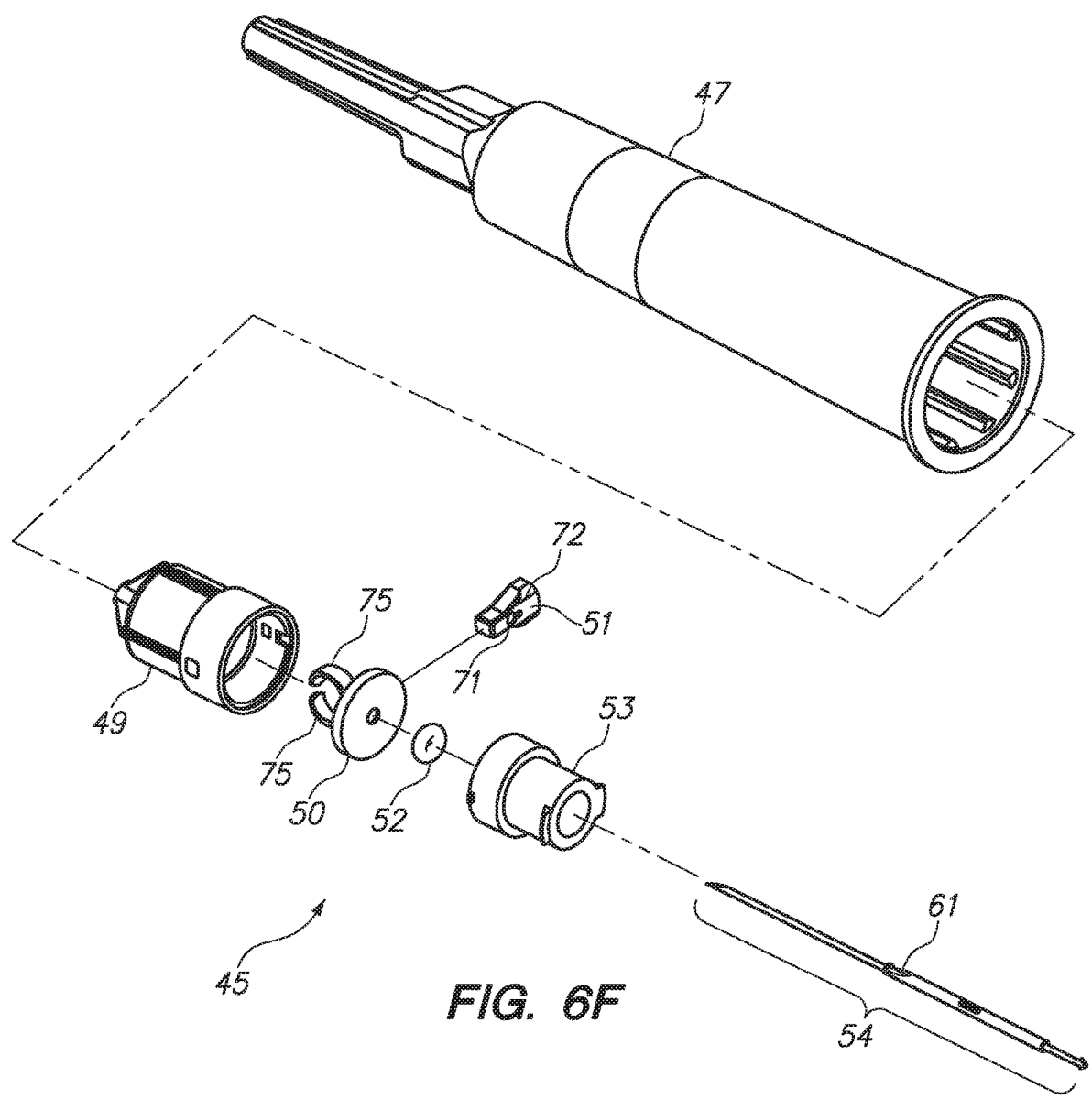
Figure 6G:
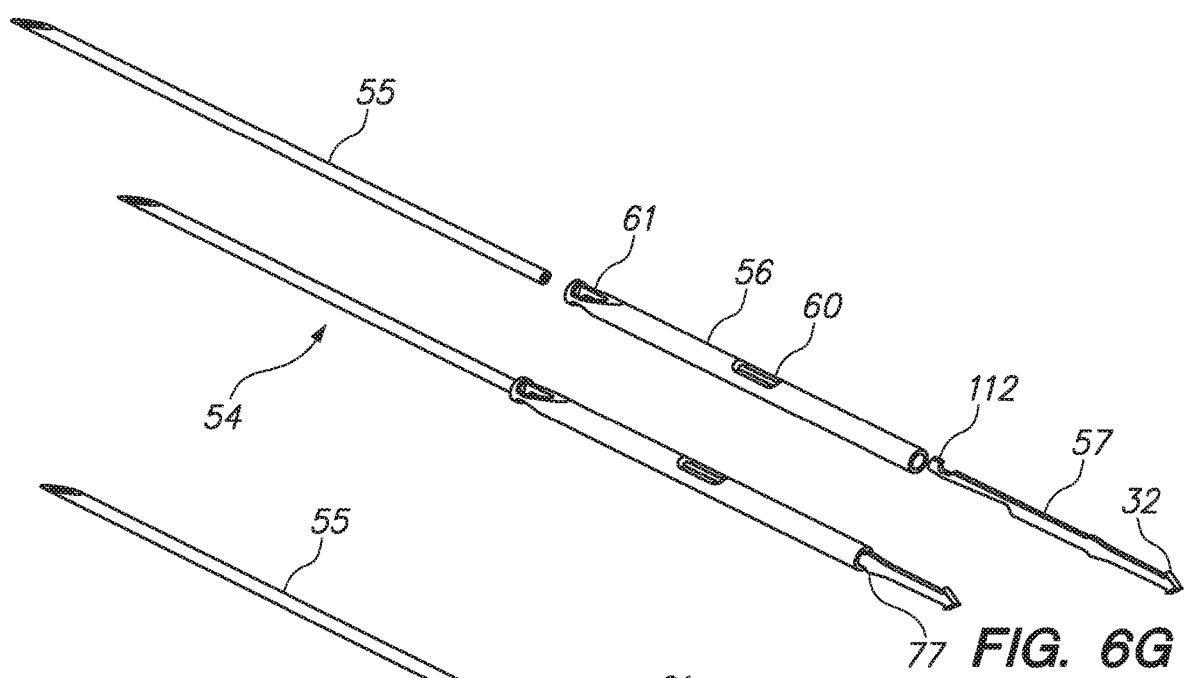
Figure 6H:
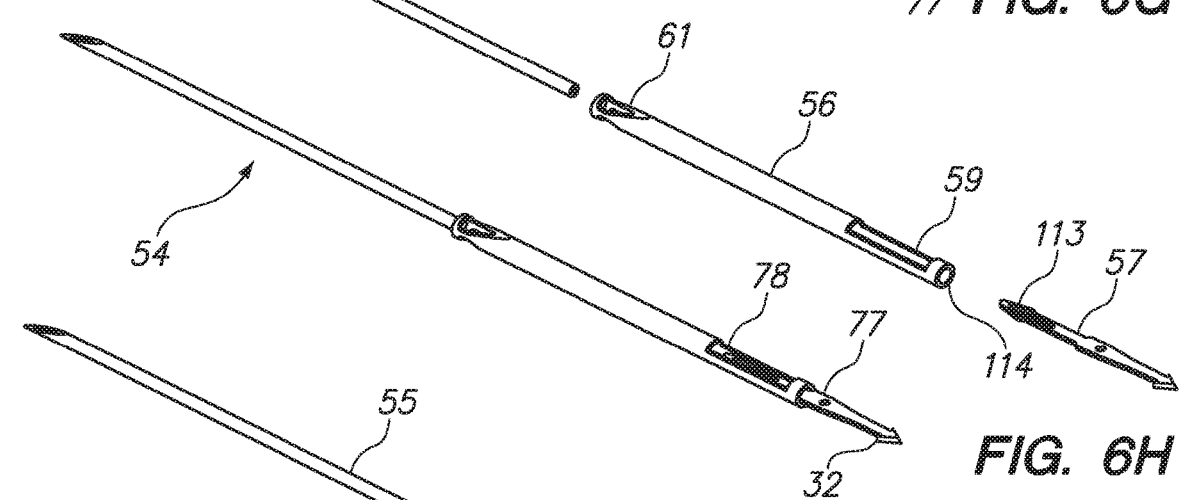
Figure 6I:
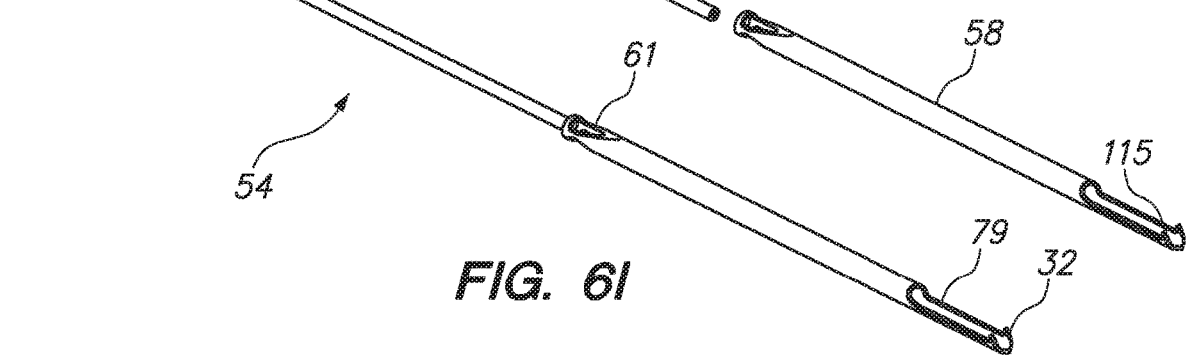

Referring to FIGS. 6E-6I, a needle assembly (45) is coupled within a needle cover (47) to hold the needle assembly inside of the cover during shipment and be released upon installation of the needle assembly onto the luer lock adapter of the syringe. The needle assembly to needle cover connection may comprise, for example, one or more of the following: snap fit, bayonetted connection, press fit, and/and screw on connection. The needle cover also may have a rim (110) which may be used to attach a sterile barrier to maintain the sterility of the needle for shipment. A spacer component also may be used to retain the needle (45) inside of the needle cover (47) during shipment. FIG. 6F is an exploded view of the needle assembly (45) which is constructed of a nose cone (49), needle latch (50), door (51), seal (52), female luer base (53), and needle (54). The nose cone (49) may be configured to snap onto the female luer base (53) to contain the other components. The needle latch (50) may comprise flexible arms (75) which grasp the needle (54) and can be flexed to release the needle. The flexible arms (75) preferably are configured to grasp the needle (54) at a notch feature (61). In the grasped state, the needle (54) is disposed inside the central lumen of the nose cone (49), needle latch (50), seal (52), and female luer base (53). The door (51) preferably is aligned so that the hole (72) is aligned with the central axis of the needle, and the door is located inside the flexible arms (75) of the needle latch. The flexible arms (75) may be flexed to release the needle (54) by applying an axial force to the needle, forcing the door forward and spreading the flexible arms (75) allowing the arms to release the needle. This allows the needle to be retracted by one of the methods shown in this document. Once the needle (54) is retracted and no longer engages the hole in the door (72), the door is forced by the flexible arms (75) laterally, misaligning the hole (72) with the axis of the needle, preventing the needle from being re-advanced. The seal (52) provides a barrier to drug leakage around the periphery of the needle (54). This seal is shown as an elastomeric O-ring, but other seals such as a septum, or packed silicone grease seal may be used. FIGS. 6G-6I are different possible constructions of the needle (54). A needle (54) constructed of a cannula (55), cannula hub (56), and at least one anchoring element, or barb (57). The at least one anchoring element (57) is intended to penetrate and grasp onto the rubber stopper of the syringe. The at least one anchoring element (57) may have plunger engaging projections (32), or may be smooth, and generally is configured to resist pullout subsequent to being at least partially pierced into at least a portion of a stopper member. The anchoring element (57) may be formed from a piece of sheet stock material, such as a metal selected from the group consist of stainless steel, cobalt-chrome alloy, and titanium, and may define a geometry such as a barb, a skive cut, a hook geometry, and/or an arrowhead geometry. In one embodiment these components comprise a metal such as stainless steel, or titanium; in another embodiment they also may comprise polymer or glass. The depicted cannula (55) is bonded to the cannula hub (56), such as by using one or more of the following: adhesive, epoxy, solder, braze, weld, laser weld, friction weld, press fit, or mechanical swage. In another embodiment the needle (54) may be manufactured as a single-piece construction. Referring to FIG. 6G, the barb or anchoring element (57) may be constructed with a latch (112) which engages with a slot (60) to retain the barb. A fluid Passage (77) is maintained around the barb in the depicted configuration so the injection fluid is not obstructed. The slot (60) also serves to expel the air bubble from the syringe body prior to giving the injection. Referring to FIG. 6H, the barb (57) is constructed with a flexible structure (113) which allows for a press-fit into the ID of the cannula hub (114) to retain the barb. Adhesive may also be placed on the flexible structure (113) to retain the barb inside the cannula hub (56). Fluid Passages (77) and (78) are maintained around the barb so the injection fluid is not obstructed. Referring to the embodiment of FIG. 6I, the barb (115) may be constructed integral to the cannula hub (58). A fluid Passage (79) is maintained around or through the barb so the injection fluid is not obstructed. A notch (61) is formed in the cannula hub (58) to engage with the needle assembly and fix in place the needle (54) during injection. This notch may also be constructed by attaching a ring about the cannula, such as by employing adhesive, press fit, or welding techniques. Alternatively, other needle to stopper attachment methods may be used, such as: suction attachment between the cannula hub and the stopper, or a bare needle which is sharp on both ends without barbs. Cannula diameter sizes range from about 0.00725 inches (34 gauge) to about 0.072 inches (15 gauge) outside diameter. Cannula length sizes range from about ¼ inch to about 2.0 inch in length projecting outside of the device for injection into the patient. The cannula hub (56) may be sized so the outside diameter is smaller than the inside diameter (31 FIG. 6C) of the luer lock adapter (44 FIG. 6C) so as to slide freely within the inside diameter of the luer lock tip of the syringe. The commercially available syringe bodies have a luer lock tip with an inside diameter which measures from about 0.040" to about 0.080". The cannula hub (56) outside diameter can range from about 0.020" to about 0.079". Preferably, the cannula hub is about 0.039" in outside diameter. In the various embodiments depicted in FIGS. 6H-6I, for example, the needle may define a drug passageway therethrough that has a proximal entrance which is located distal to a distal end of the stopper member when the sharpened (i.e., barbed, etc) proximal end of the needle assembly is penetrated into the stopper member.

Figure 6J:
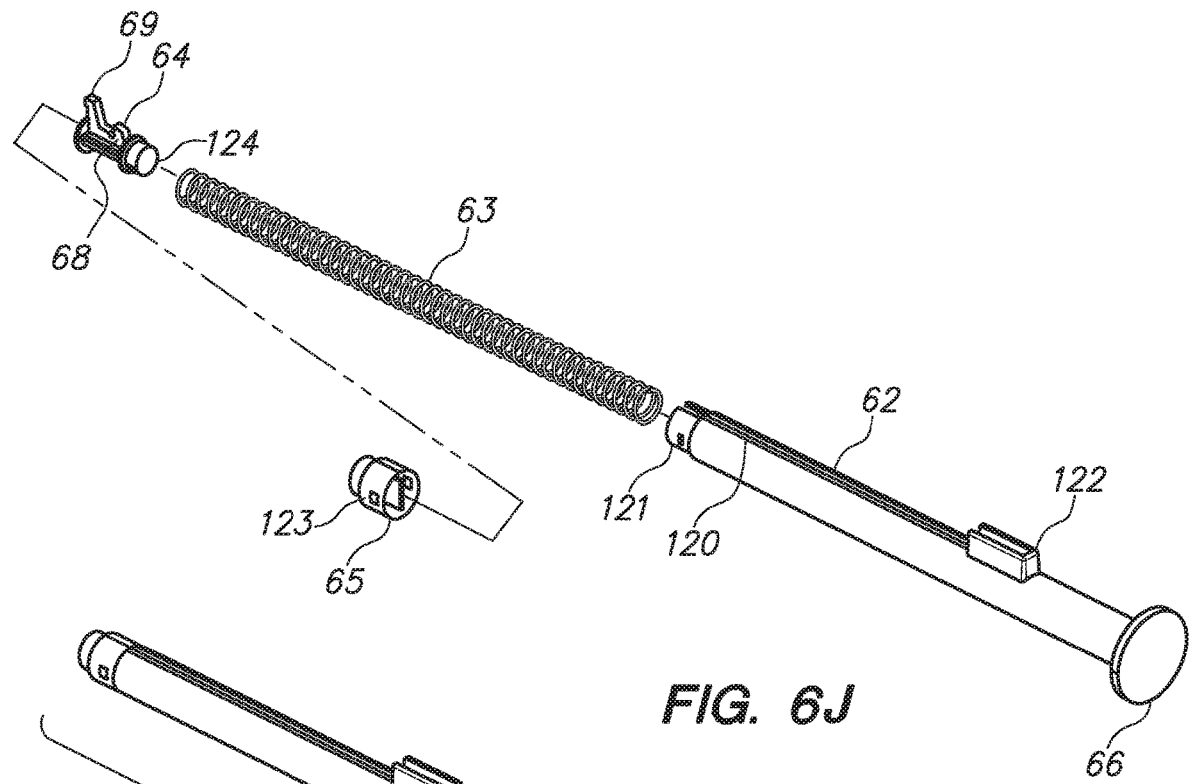
Figure 6K:
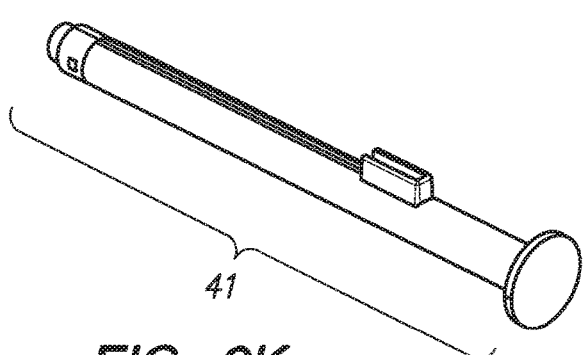
Figure 6L:
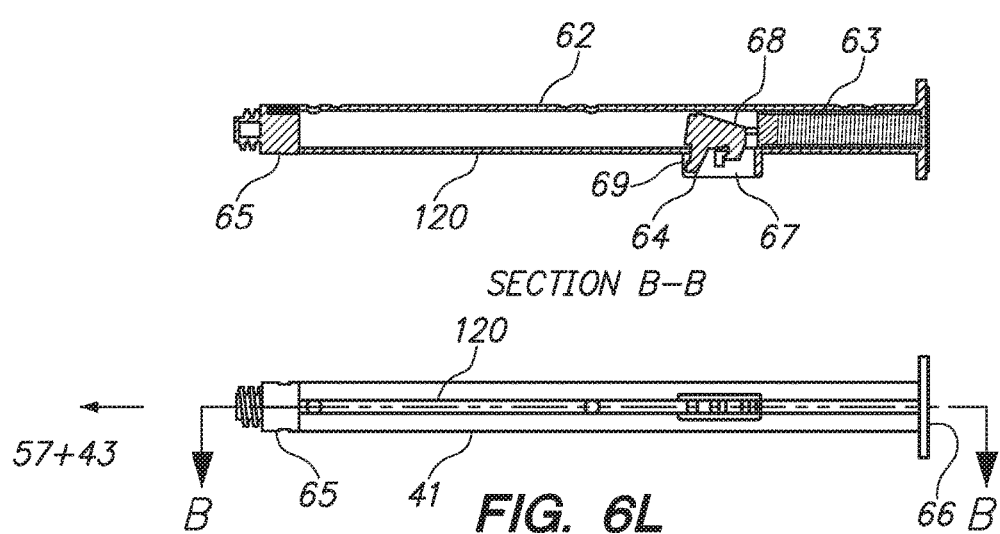

Referring to FIGS. 6J-6L, a plunger assembly (41) may comprise of a plunger base or plunger member body (62), latch member (64), retraction element, or energy-storing member, (63), and plunger tip (65). FIG. 6J is an exploded view of the plunger (41). The plunger base (62) is a hollow tubular structure with a latch mating surface (67) located near the thumb pad feature (66). The plunger assembly (41) may have a threaded distal tip for intercoupling into a stopper member, and may comprise a hollow recess configured to allow a needle member proximal end to fully penetrate a stopper member. The thumb pad (66) closes off one end of the tubular structure creating a location for a retraction element (63) to be retained. Disposed within the plunger member body (62) is a latch member (64), which retains the retraction element or energy-storing member (63). The plunger member body (62) may define an interior volume configured such that an energy-storing member or retraction element (63) may be housed substantially within the plunger member body interior volume. With a spring-type energy-storing member, the spring member may comprise a single generally helically-shaped coil. In another embodiment, the spring member may comprise a plurality of generally helically-shaped coils, which may, for example, be co-axially aligned, longitudinally parallel aligned, or both co-axially aligned and longitudinally parallel aligned. In an embodiment wherein the spring member comprises both co-axially aligned and longitudinally parallel aligned spring elements or coils, the spring elements or coils may be helically wound with opposite winding directions relative to each other to prevent coil interference upon compression of the coils.

Distal to the latch mating surface (67) is a clearance slot (120) which allows the latch member (64) to travel towards the plunger screw (65) upon release of the retraction element (63). The plunger screw (65) is coupled to the tip of the plunger base (62) with a snap connection between tabs (121) and slots (123). Other attachment methods of the plunger screw (65) to the plunger base (62) include but are not limited to: a threaded connection, a bonded connection, a welded connection, and/or integral construction. A latch guard (122) may be configured to protect the latch from inadvertently being activated. The depicted latch member (64) has a latch hook (68), a trigger element (69) and a retraction element engaging feature (124). The latch member may comprise a polymer material, such as polyetherimide, peek, and/or polyamide. Similarly, the various components of the plunger may comprise a polymer material, such as polyetherimide, peek, and/or polyamide. FIG. 6K depicts a fully assembled view of the plunger (41). FIG. 6L illustrates a cross sectional view of the plunger (41) showing the latch member (64) installed in place to retain the retraction element or energy-storing member (63) in a compressed condition prior to retraction of a needle. The latch has a hook (68) which engages a mating surface (67) inside the plunger body (62) to retain the retraction element inside the plunger in a compressed state. An alternate configuration may have the retraction element (63) on the outside of the plunger shaft. The depicted latch member (64) has a trigger element (69) which acts to dis-engage the hook (68) from the mating surface (67) releasing the retraction element (63) to expand. The latch is triggered to release when an axial force is applied to the trigger (69). This axial force is applied at the bottom of the injection stroke by contact with the handle contact surface (70 FIG. 6S). The released retraction element forces the latch to move axially along the slot (120) in the plunger base (62) this movement is reacted by the latch contact surface (70) of the handle (42) shown in FIG. 6M, forcing the plunger to move retrograde, retracting the needle (54 FIG. 6F) which is coupled to the stopper (43) which is coupled to the plunger screw which is coupled to the plunger. The retracting element shown here is a metal spring, but other compressible elements are envisioned. The energy-storing member, or retraction element, (63) may comprise one or more helical springs, or a solid pellet member, and may comprise materials such as a polymer, elastomer, or rubber material. For example, an energy storing member spring may comprise a material selected from the group consisting of: stainless steel, carbon steel, beryllium copper alloy, nickel-titanium alloy, chrome-silicon alloy, and cobalt-nickel alloy. Alternatively a spring energy-storing member may comprise an elastomeric polymer, such as a material selected from the group consisting of: a styrenic polymer, a co-polyester polymer, polyurethane, polyamide, a polyolefin blend, a polyolefin alloy, a polyolefin plastomer, a polyolefin plastomer, and rubber. A solid pellet energy-storing member may comprise an elastomeric polymer selected from the group consisting of: a styrenic polymer, a co-polyester polymer, polyurethane, polyamide, a polyolefin blend, a polyolefin alloy, a polyolefin plastomer, a polyolefin plastomer, and rubber. The plunger base (62), latch (64), and plunger tip (65) may be constructed of a polymer such as nylon, Ultem, polyetherethreketone, polyethylene, polypropylene, COC, COP, glass or carbon fiber filled polymers, or other filled polymer composites. Alternative materials for the latch, plunger base, or plunger tip are metals, or other structural materials.

Figure 6M:
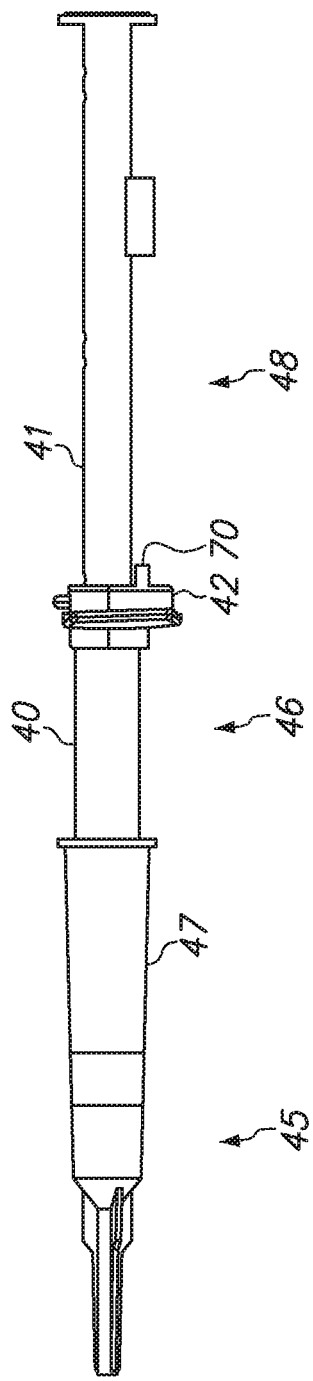
Figure 6N:
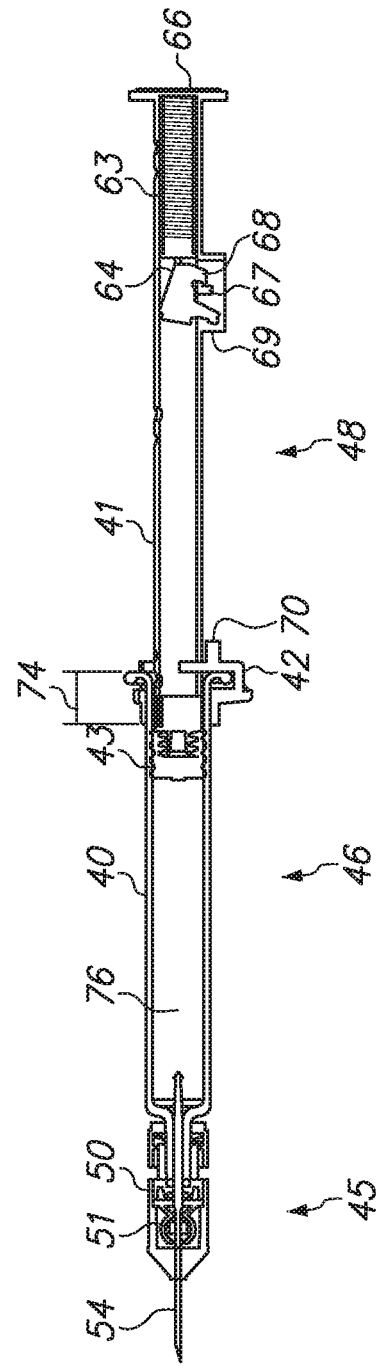
Figure 6S:
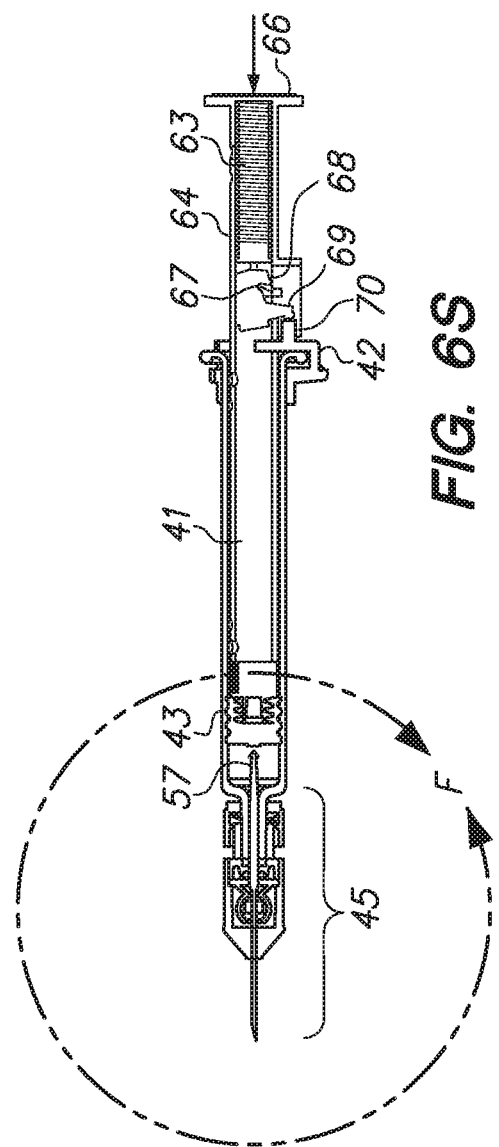
Figure 6T:
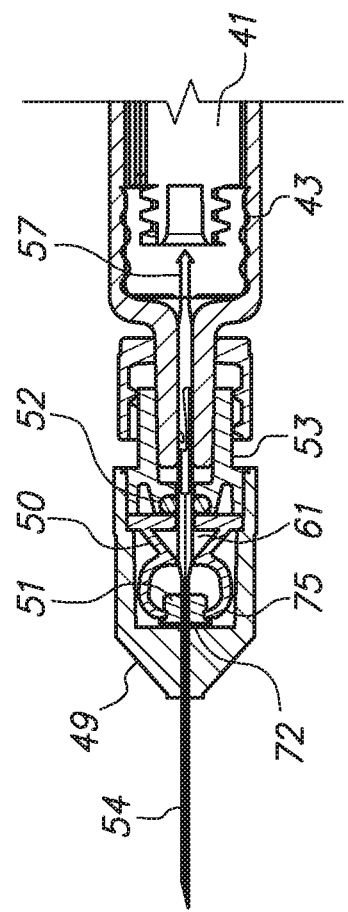
Figure 6U:
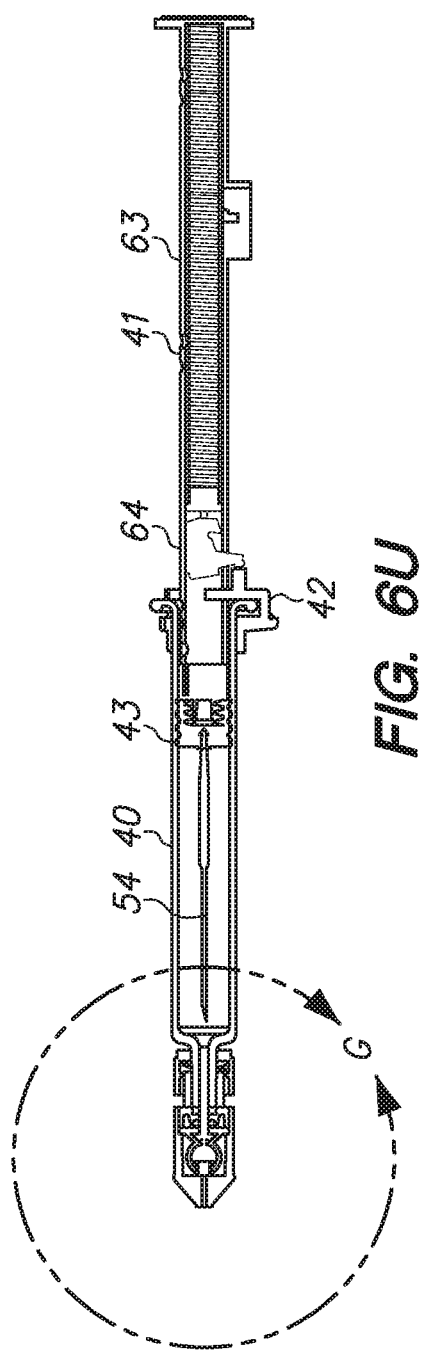
Figure 6V:
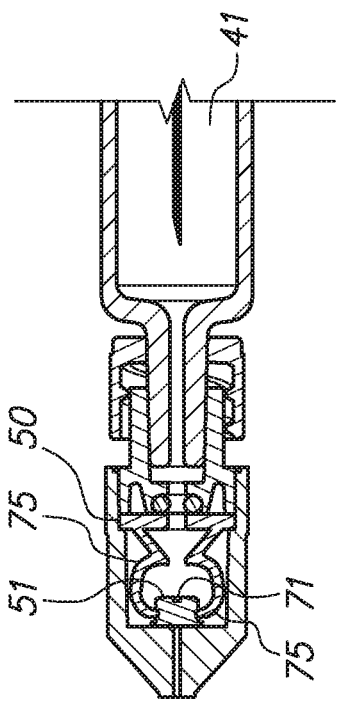

Referring to FIGS. 6M-6V, a sequence of injection for one embodiment is illustrated. FIG. 6M is a side view showing the syringe body assembly (48) with syringe body (46), handle (42), and plunger (41) installed. The needle cover (47) guided the needle (45) into the syringe tip. FIG. 6N shows a cross section of the device during use. The needle (45) is coupled to the syringe body assembly (48). The drug to be delivered (76) has been pre-loaded inside the syringe barrel (40) prior to syringe assembly. The needle assembly (45) is grasping the needle (54) with the needle latch (50) and door (51) aligned to retain the needle during shipping, handling, assembly, injection, and or withdrawal from the patient. The syringe stopper (43) is located at the end of the plunger (41), and is able to be retracted over the distance (74) in the event that aspiration of the needle is necessary to identify if the injection site is in a blood vessel. The retraction element (63) is restrained by the latch (64) in a compressed state. The person administering the injection applies an axial force on the plunger thumb pad (66) and the handle (42) to force the liquid through the needle and into the patient. FIG. 6O depicts a cross section of the device illustrating aspiration of the needle. A force may be applied to the thumb pad (66) to pull the plunger (41) and stopper (43) retrograde, reducing the distance (74) and creating a slight vacuum at the tip of the needle, aspirating the needle. FIG. 6P illustrates the needle being grasped by the needle latch (50) via the flexible arms (75) interfacing with the notches (61) in the cannula hub. FIG. 6Q illustrates the progression of giving the injection. A force may be applied antegrade to the thumb pad (66) moving the plunger (41) and stopper (43) to force the drug (76) out through the needle. FIG. 6R shows the needle being retained during the injection. FIG. 6S illustrates the completion of the injection. The plunger (41) has been fully advanced. The needle is released by forcing the door (51) into the needle latch arms (75), spreading the arms and releasing the needle (54) for retraction. The stopper (43) has been pierced by the barb (57). The Barb (57) is configured to couple to the stopper once pierced, enabling retraction of the needle upon retrograde motion of the stopper (43). The latch (64) is rotated, by contact between a latch contact surface (70) projecting from the handle (42) and the latch trigger element (69). The latch hook (68) dis-engages from the mating surface (67), releasing the retraction element (63) to apply an axial force to move the plunger (41), and stopper (43) retrograde, retracting the coupled needle (54) from the tip of the syringe. Latch hook disengagement may occur simultaneously with the end of the injection stroke, or may occur before the end of the injection stroke. The user may now remove their thumb from the thumb pad (66) to allow the plunger to move retrograde, retracting the needle. Alternatively, the user may retain thumb contact with the thumb pad (66) to control retraction speed. FIG. 6T illustrates one embodiment of a needle release mechanism. The barb (57) of the needle (57) contacts and couples to the stopper (43) which is coupled to the plunger (41). The coupling of the barb (57) to the stopper (53) may be created by stabbing the barb into the stopper. Other suitable methods for coupling the barb to the stopper include but are not limited to: vacuum, adhesive, hooking, and/or a Velcro type connection. The needle (54) is forced forward by the stopper (43) during the coupling action and contacts the door (51) with the distal end of the cannula hub (56) and pushes the door into engagement with the flexible arms (75) of the needle latch (51). The flexible arms are expanded laterally, allowing the notch (61) of the needle (54) to move axially upon retraction of the needle (54) by the retraction element (63) coupled to the plunger (41) coupled to the stopper (43). FIG. 6U illustrates the retracted needle (54) inside the cylinder (40). The retraction element (63) has forced the plunger (41) rearward which retracts the needle (57) which is coupled to the stopper (43) and the plunger (41). The rate of retraction of this needle is damped by the friction between the stopper (43) and the cylinder (40). Different levels of lubrication of the stopper (43) can be used to enable fast or slow retraction of the needle. FIG. 6V illustrates the position of the door (51) once the needle is retracted. The flexible arms (75) force the door hole (72 FIG. 6F) out of alignment with the axis of the needle, preventing re exposure of the needle by the user. A needle catching feature (71) is now aligned with the needle axis, preventing the needle from being re-exposed by accidental advancement of the plunger.

Figure 7A:
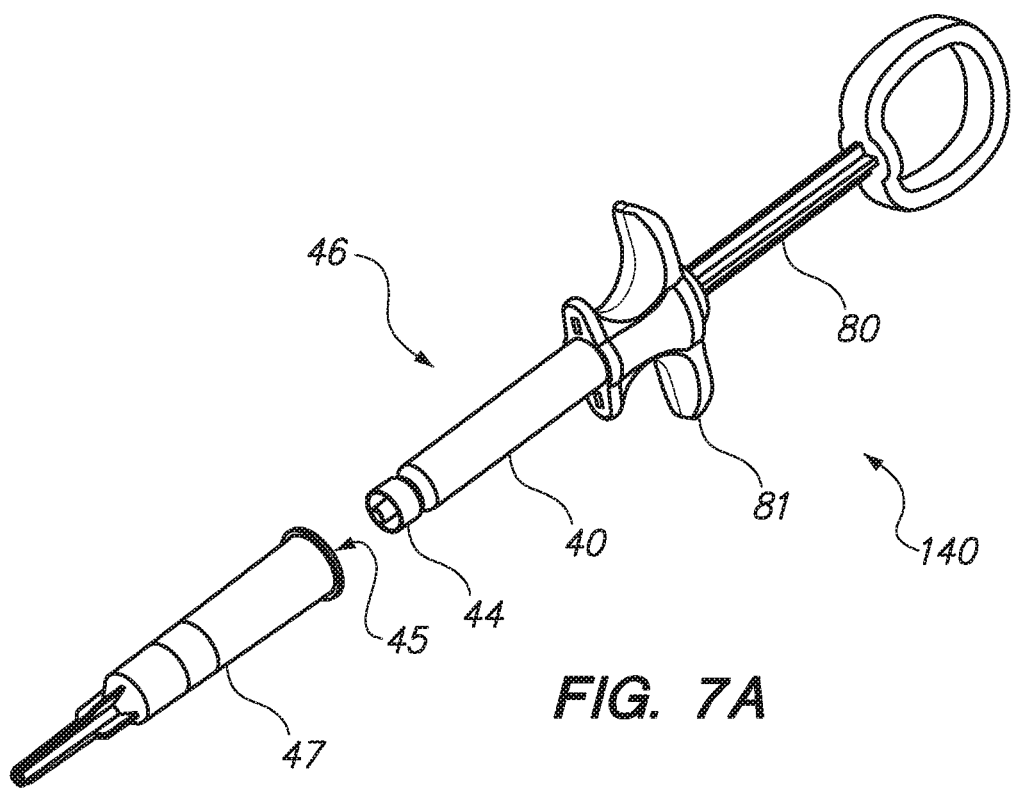

Referring to FIGS. 7A-LD, a safety syringe embodiment is depicted wherein a syringe body is connected to a plunger, a handle, and a needle to create a manual activated safety syringe. FIG. 7A is an illustration of a syringe and plunger assembly (140) which may comprise a syringe body (46) connected to a handle (81) and a plunger member (80). The syringe body may be provided empty or pre-filled with drug prior to assembly. A needle (45) is shown disposed within a needle cover (47). In the depicted embodiment, the needle is to be coupled to the syringe body (46) using the luer lock tip (44) coupled to the cylinder (40). Alternatively, the handle (81) and plunger member (80) may be supplied alongside the syringe body (46) and assembled by the user at the point of care. Also, the needle (45) may be pre-coupled to the syringe and plunger assembly (140) by the manufacturer.

Figure 7B:
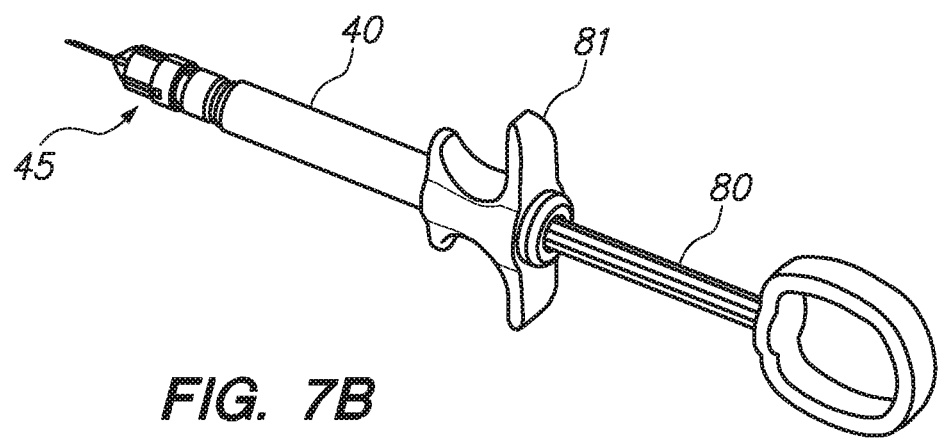
Figure 7C:
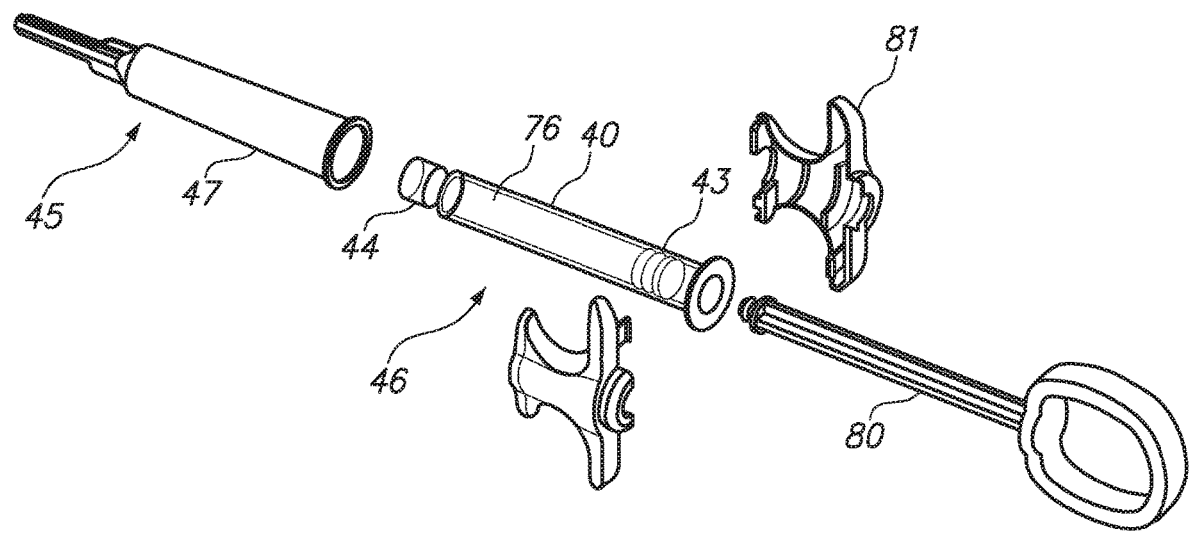

FIG. 7B is an illustration of the safety syringe assembled and ready to commence injection. The depicted needle (45) is coupled to the syringe body (46), with the handle (81) and plunger member (80) coupled. FIG. 7C is an exploded view of the device. The syringe body (46) comprises a cylinder (40), a luer lock tip (44), and is configured to be interfaced with a stopper member (43). Drug (76) can be pre-filled inside the cylinder and retained with the stopper (43). Alternatively, drug can be filled into the syringe at the time of use from a medicine vial. The plunger member (80) is screwed into the stopper (43). The handles (81) are coupled to the syringe body (46). The needle (45) inside of the needle cover (47) is then coupled to the syringe body (46).

Figure 7D:
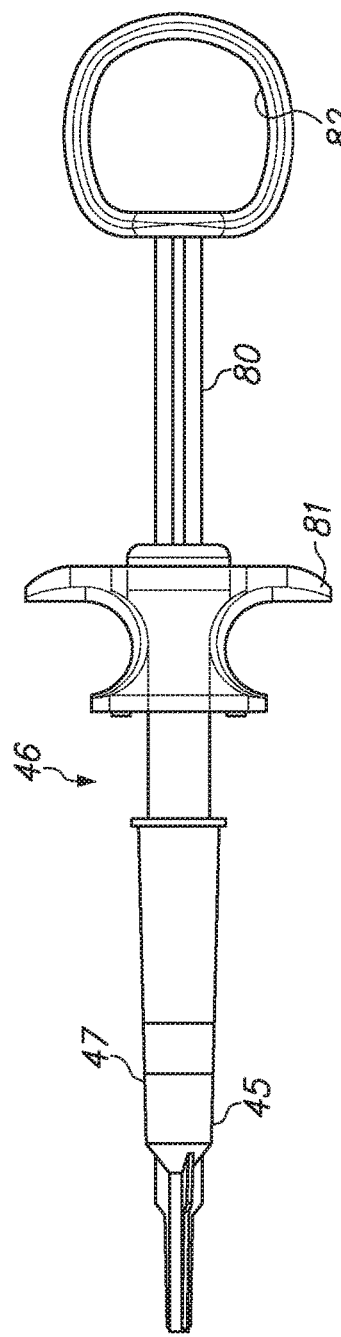
Figure 7E:
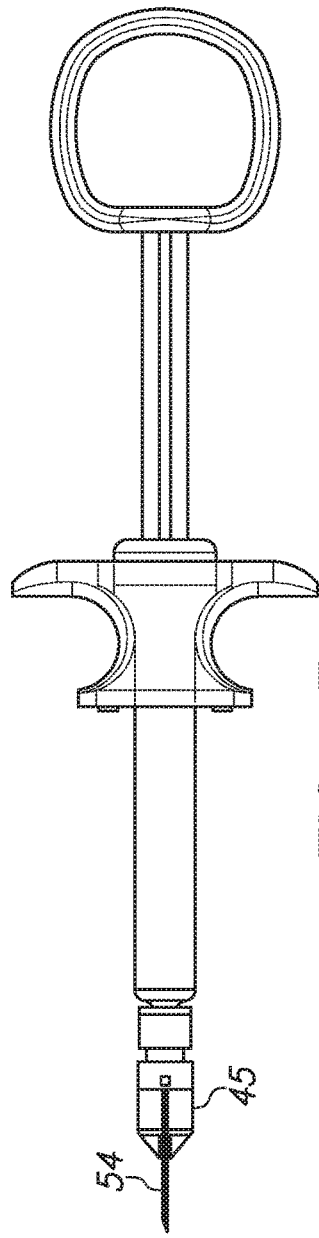
Figure 7F:
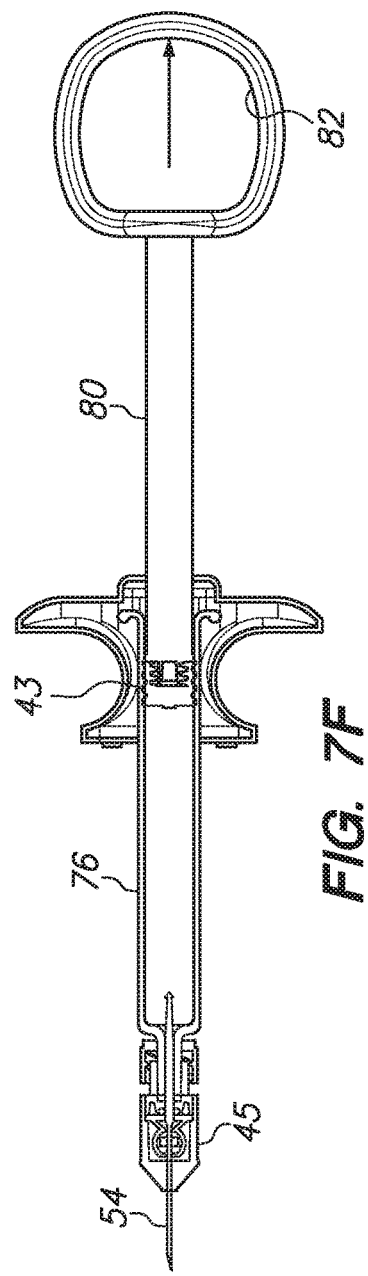
Figure 7G:
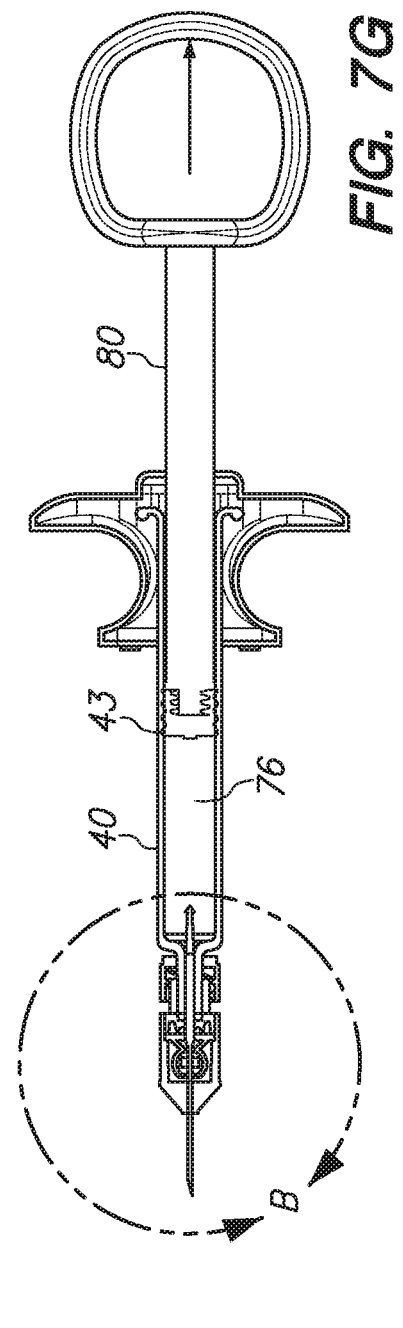
Figure 7H:
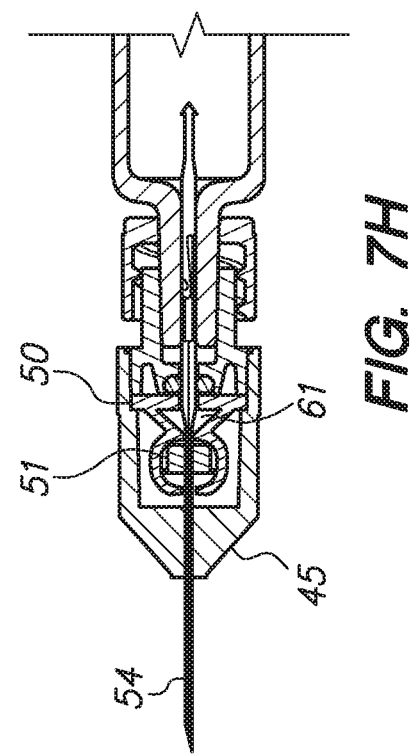
Figure 7K:
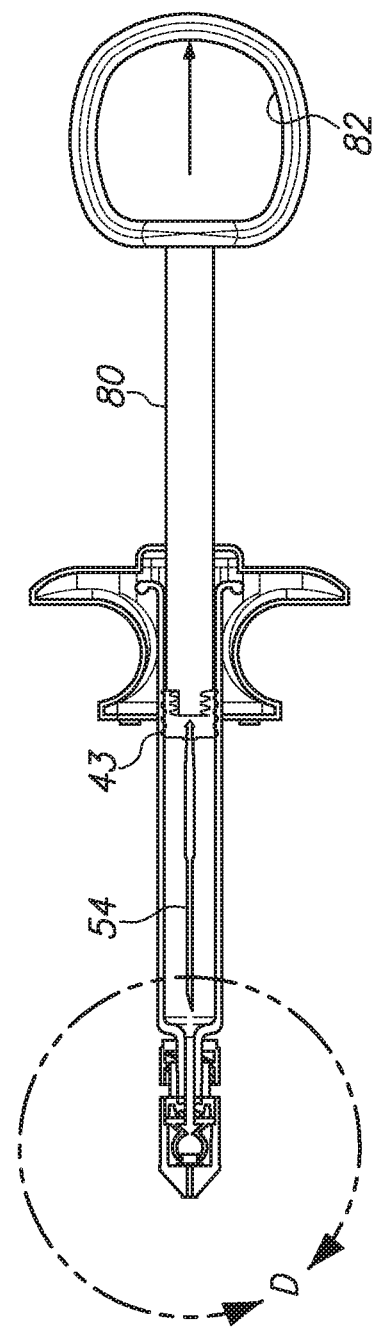
Figure 7L:
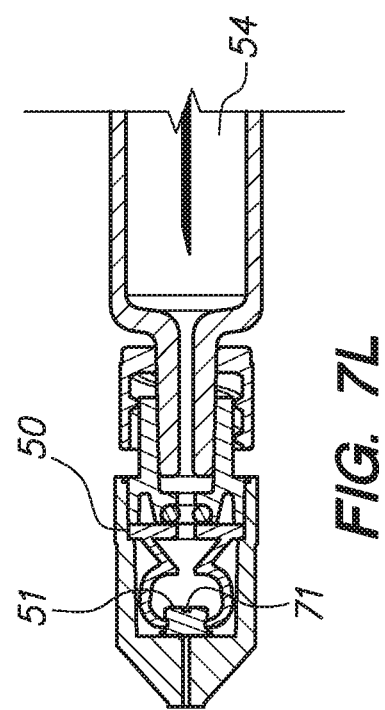

Referring to FIGS. 7D-7L an embodiment of a sequence for giving an injection is shown. FIG. 7D shows the syringe body (46) with the handle (81) and plunger member (80) installed. The plunger has a ring (82) for applying force to the stopper. The needle assembly (45) is inserted into the tip of the syringe using the needle cover (47) to guide the alignment. FIG. 7E shows the needle assembly (45) installed with the needle (54) ready for giving the injection. FIG. 7F shows aspiration of the needle (54) by applying a retrograde force to the plunger ring (82). This action pulls the stopper (43) retrograde and creates a slight vacuum at the needle tip to determine if the needle tip is in a blood vessel. Alternatively, the plunger could have a thumb pad (66 FIG. 6J) type construction and or have a smooth shaft for grasping and manually retracting the needle. FIG. 7G illustrates the injection of the medicine (76) into the patient. FIG. 7H illustrates the needle assembly during the injection. The needle (54) is captured at notch (61) by the needle latch (50) and door (51). FIG. 7I illustrates the completion of the injection and the release of the needle. Force is applied to the end of the plunger (80), forcing the stopper (53) to reach the end of the syringe barrel (40) expelling the drug. The stopper (43) applies a force to the needle (54) through the barb (57) to force the needle and door (51) forward, unlatching the needle latch (50). The barb (57) of the needle (54) penetrates the stopper (43), coupling the needle to the plunger rod (80). Penetration of the stopper may be partial or full. FIG. 7J is a larger view of the needle in the unlatched position. The door (51) is pushed forward by the plunger force reacted through the cannula hub (56) and the barb (57). The door (51) forces the needle latch (50) to disengage from the notch (61), allowing the needle to be released. The door (51) has a hole (71) which is aligned with the needle (54). FIG. 7K shows the application of a retrograde force to the ring (82) of the plunger (80), retracting the stopper (43) and with it the coupled needle (54). FIG. 7L illustrates the motion of the door (51) upon clearance by the needle (54). The door slides lateral so the hole (72 FIG. 6M) is no longer aligned with the needle. A needle catching feature (71) is now aligned with the needle axis, preventing the needle from being re-exposed by accidental advancement of the plunger. At this time the plunger (80) can be unscrewed from the stopper (43) and discarded. Alternatively, the plunger can be frangible, and broken off for disposal and to further prevent accidental needle exposure.

Figure 8A:
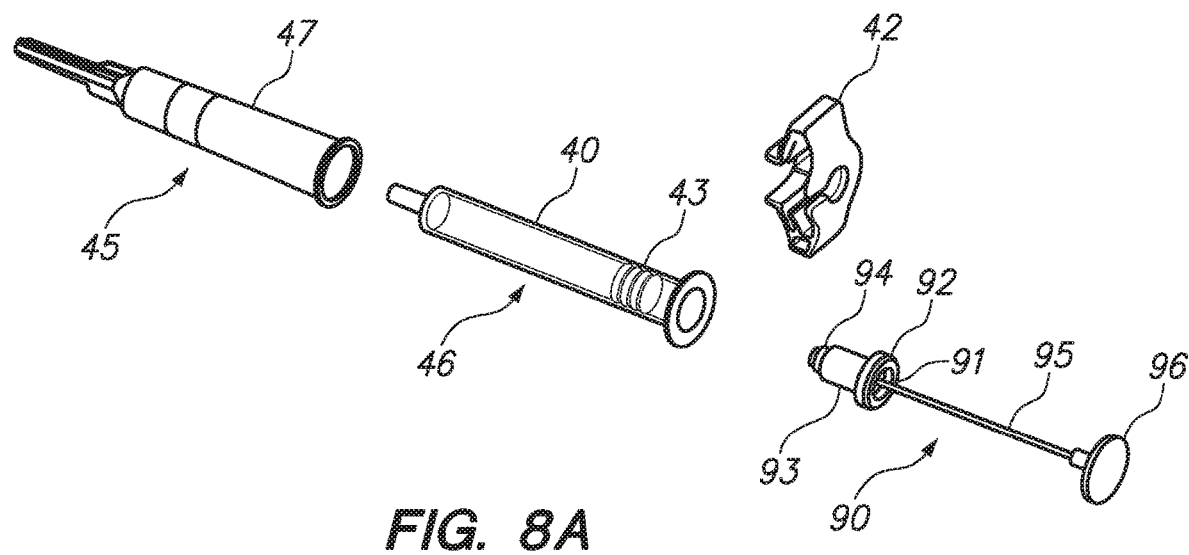
FIGS. 8A-8L illustrate various aspects of one embodiment of an adaptable safety syringe assembly in accordance with the present invention, wherein the needle is automatically retracted upon giving an injection.
Figure 8B:
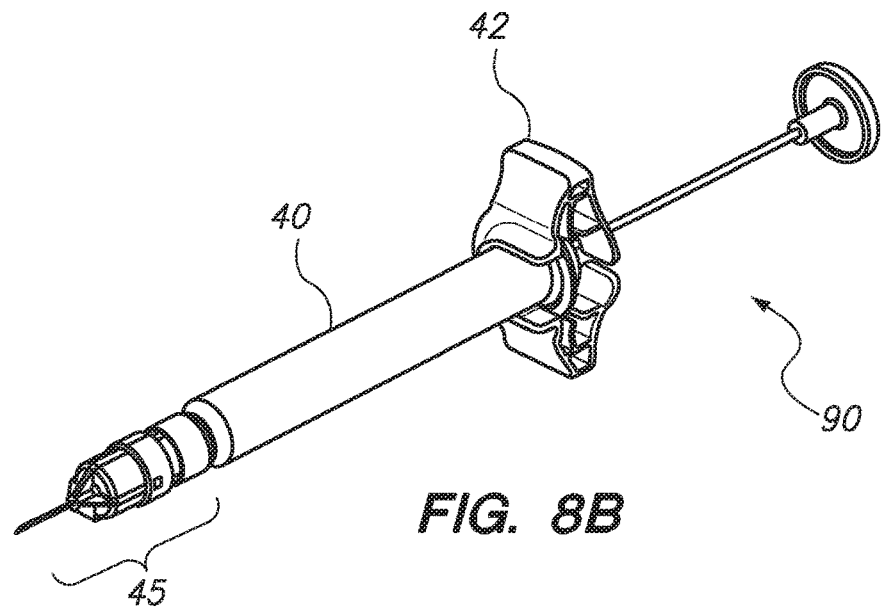
Figure 8C:
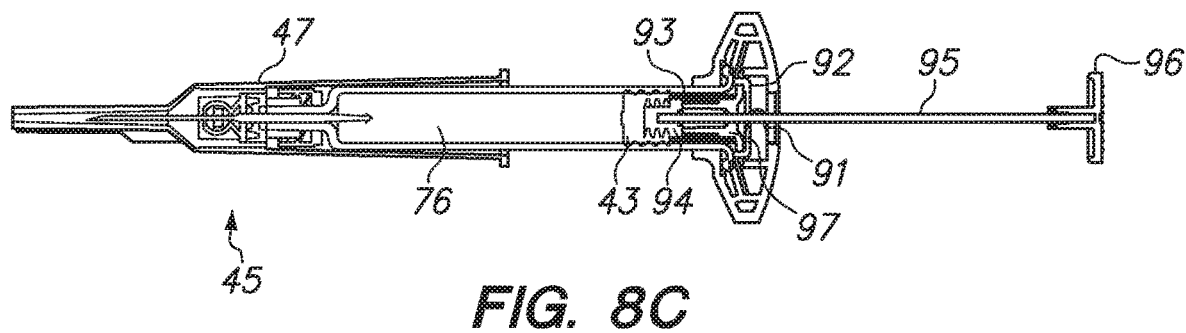
Figure 8D:
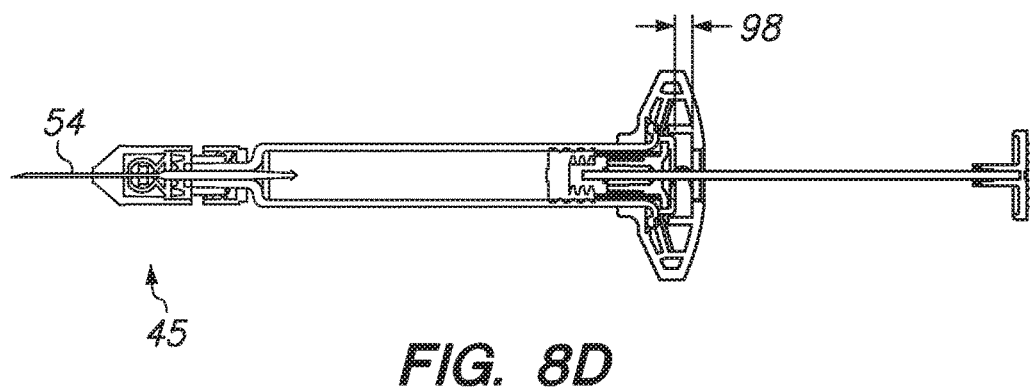
Figure 8E:
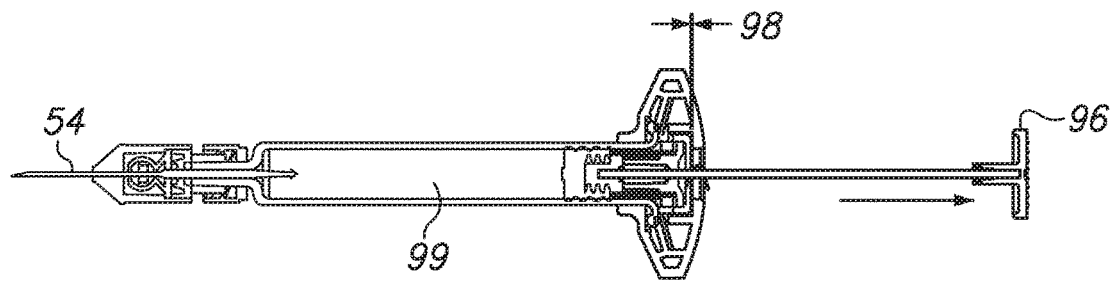
Figure 8F:
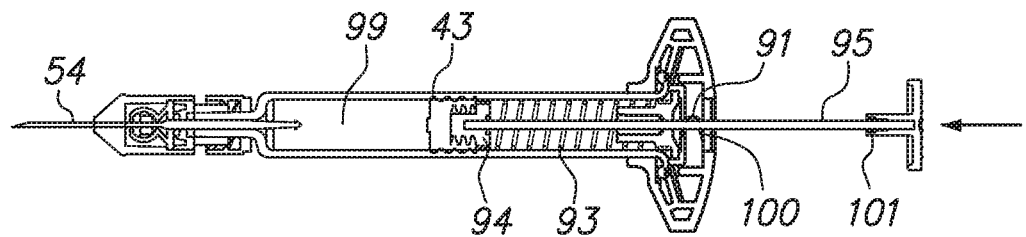
Figure 8G:
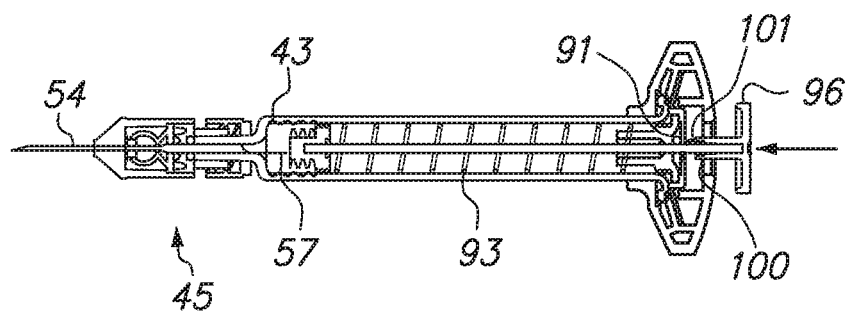
Figure 8H:
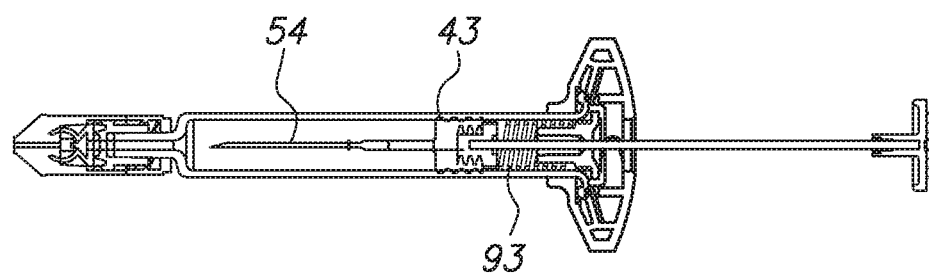
Figure 8I:
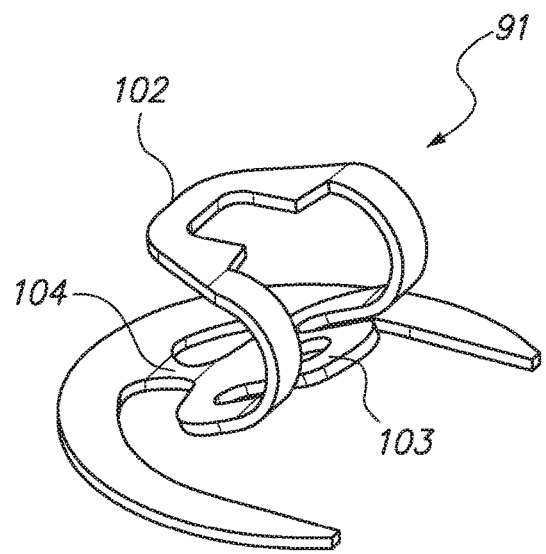
Figure 8J:
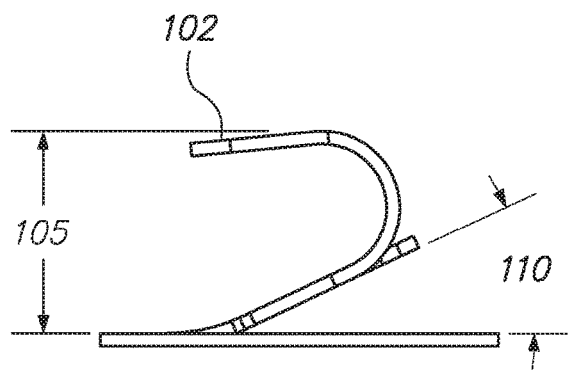
Figure 8K:
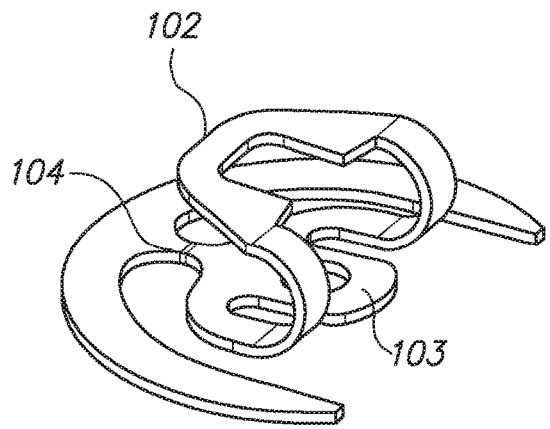
Figure 8L:
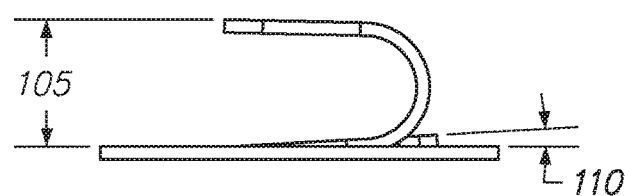

Referring to FIGS. 8A-8L, various aspects of an alternate embodiment of an automatically retractable needle safety syringe are illustrated. FIG. 8A is an exploded view of a syringe with a syringe body (46) comprising a cylinder (40) which is coupled to a stopper member (43). A needle assembly (45) is disposed within a needle cover (47). A plunger (90) is shown comprised of a plunger screw (94), retraction element (93), brake (91), brake retainer (92), plunger rod (95) and thumb pad (96). FIG. 8B is an alternate view of the completed syringe ready for injection. The needle assembly (45) is installed on the tip of the syringe (40) with the plunger coupled to the stopper (43) and the handle (42) installed. FIG. 8C is an illustration of the syringe with the needle cover (47) and needle assembly (45) installed. The proximal end of the device shows the syringe filled with drug (76) the stopper in place (43) the plunger screw (94) installed in the stopper, the retraction element (93) is shown coupled to the plunger screw and the proximal base (97). The brake (91) is coupled to the proximal base (97) with the brake retainer (92). The plunger rod (95) is coupled to the plunger screw (94), the thumb pad (96), and is disposed through the hole in the brake (91). FIGS. 8D and 8E shows aspiration of the needle by retracting the stopper (43) over a distance (98) with application of retrograde force to the thumb pad (96). FIG. 8F shows the injection of the fluid by application of a force antegrade to the thumb pad (96). This force is transmitted through the plunger rod (95) to move the stopper (43), expelling the liquid through the needle (54). The retraction element (93) is stretched, storing energy to be used later to retract the needle (54). The brake (91) is configured to have two configurations, "braking", and "free". In the "braking" configuration, the brake will allow antegrade motion of the plunger rod (95), and resist retrograde motion. While in the "free" configuration the brake will allow both antegrade and retrograde motion. The brake prevents the plunger from moving retrograde if the user was to remove their thumb from the thumb pad. This is useful in the event that a single medication is to be administered over multiple injection sites, or if only a partial dose is required. The user could expel the remaining dose and trigger the safety mechanism to retract the needle. The trigger mechanism to switch the brake from "braking" to "free" is crushing of the brake caused by contact between the distal surface of the thumb pad (101) and the proximal surface of the brake (100). FIG. 8G illustrates the completion of the injection. The fluid has been injected into the patient, the stopper (43) has bottomed on the syringe body. The needle (54) has been released from the needle assembly (45) and the barb (57) is coupled to the stopper (43). The brake (91) has been switched from "braking" to "free" by contact between the brake and the thumb pad surface (101). The retraction element (93) is fully stretched, storing energy to be used to retract the needle. At this time, removing the users thumb from the thumb pad allows the needle to be retracted. FIG. 8H illustrates the needle retracted into the syringe body by the stored energy in the retraction. FIG. 8I-8L illustrate the brake component. The brake (91) is comprised of a central hole (103) which is configured to be angled upward (110) and drag on a plunger shaft installed therethrough. This drag is present to resist plunger shaft motion in an upward direction while allow free motion in the other direction. The brake further comprises a necked down portion (104) which is designed to plastically deform under the application of a crushing force to the upper surface (102). This causes the brake to deform, reducing the angle (110) and causing the central hole (103) to align with the plunger shaft allowing free motion of the plunger shaft in both directions. The upper surface of the brake (102) is also intended to deform during brake disengagement to accommodate assembly tolerances allowing the retraction mechanism to perform reliably.

The systems and methods of needle retraction and guarding described above are illustrated for use in pre-filled syringes. These systems and methods are also useful in commodity syringes and pen type auto-injectors.

Figure 9:
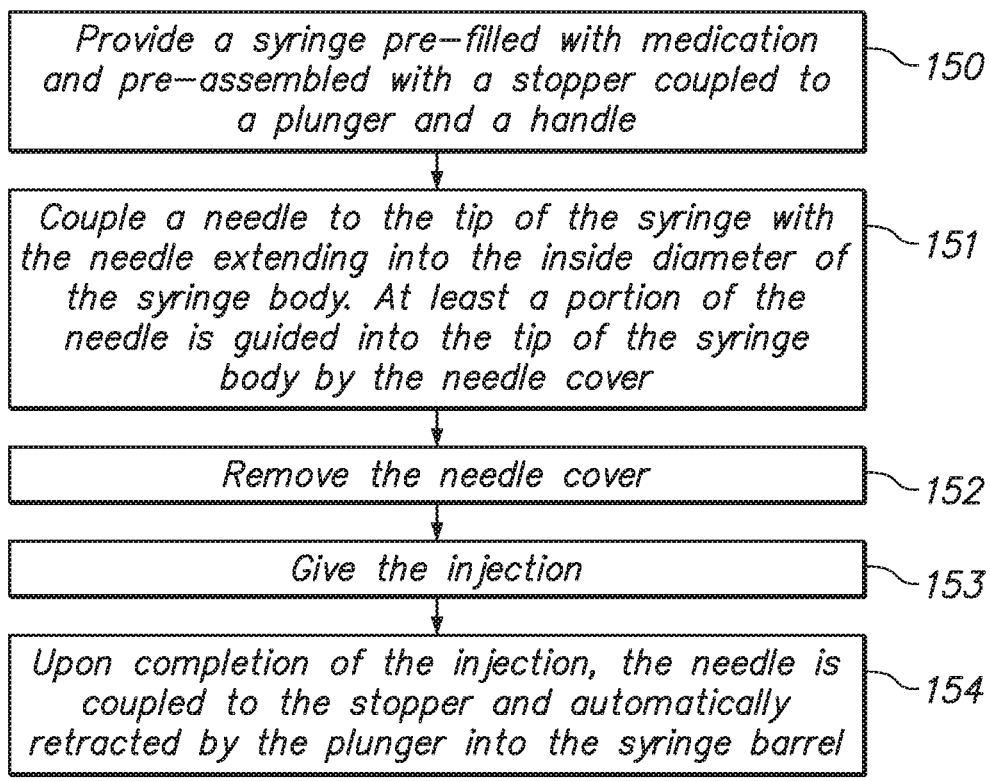
FIG. 9 illustrates various aspects of one embodiment of a process for conducting an injection using an automatic retraction safety syringe configuration in accordance with the present invention.

Referring to FIG. 9, one embodiment of a method for performing an injection is illustrated. The method involves providing a pre-filled syringe which is pre-assembled with a syringe body, plunger and handle (150). Coupling a needle to the tip of the syringe where at least a portion of the needle extends inside the inner diameter of the syringe body (151). Preferably this needle is guided into the syringe body by a needle cover, however other guiding features may be used. Also, no guide may be used, the user can visualize the needle entering the id of the syringe body. Removing the needle cover (152). Giving the injection (153). Upon completion of the injection, the needle is coupled to the stopper which is coupled to the plunger and the plunger is configured to automatically retract the needle into the syringe barrel (154)

Figure 10:
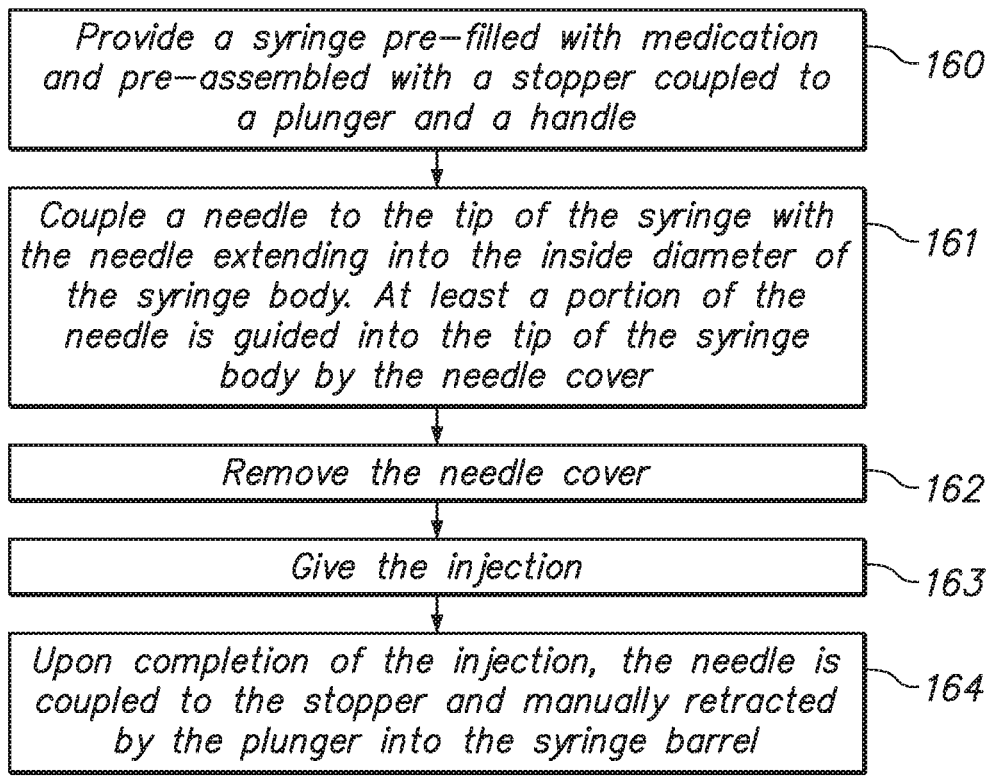
FIG. 10 illustrates various aspects of one embodiment of a process for conducting an injection using a manual retraction safety syringe configuration in accordance with the present invention.

Referring to FIG. 10, one embodiment of a method for performing an injection is illustrated. The method involves providing a pre-filled syringe which is pre-assembled with a syringe body, plunger and handle (160). Coupling a needle to the tip of the syringe where at least a portion of the needle extends inside the inner diameter of the syringe body (161). Preferably this needle is guided into the syringe body by a needle cover, however other guiding features may be used. Alternatively, no guide may be used, the user can visualize the needle entering the id of the syringe body. Removing the needle cover (162). Giving the injection (163). Upon completion of the injection, the needle is coupled to the stopper which is coupled to the plunger and the plunger is configured to manually retract the needle into the syringe barrel (164).

Figure 11:
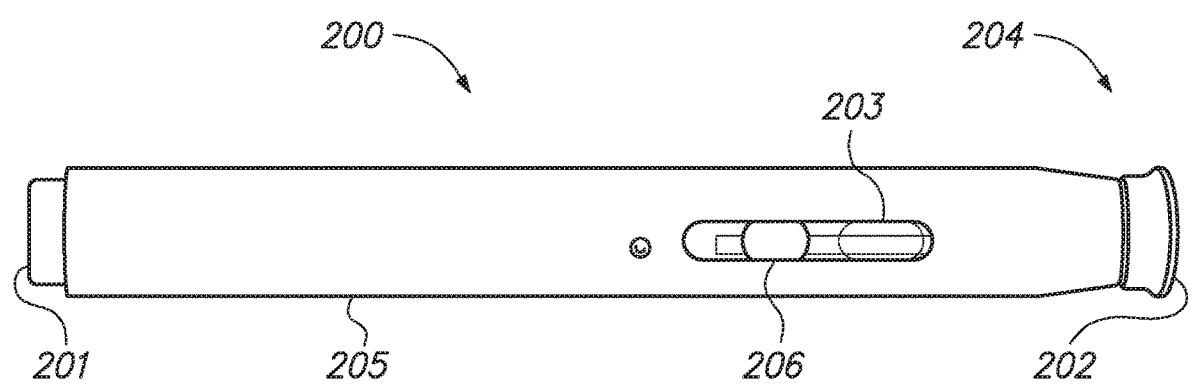
FIG. 11 illustrates other possible applications for this technology, pen type auto-injectors, and commodity syringes.

Referring to FIG. 11, one embodiment of a pen style auto injector is illustrated (200). The depicted auto injector comprises a body (205) housing an injection button (201) a medicine vial (203), with a butyl rubber stopper (206) disposed inside. A needle (204) is disposed inside a needle guard (202) at the distal tip of the device. The medicine vial (203) may be pre-filled with drug. The retractable needle mechanism (45 of FIG. 6F) and the needle geometry (54 of FIG. 6F) can be used to couple to the butyl rubber stopper (206) of the auto injector (200), while the plunger mechanism (41 of FIG. 6L) can be used in the injection button (201) creating a retractable needle auto injector.

Various exemplary embodiments of the invention are described herein. Reference is made to these examples in a non-limiting sense. They are provided to illustrate more broadly applicable aspects of the invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. Further, as will be appreciated by those with skill in the art that each of the individual variations described and illustrated herein has discrete components and features which may be readily separated from or combined with the features of any of the other several embodiments without departing from the scope or spirit of the present inventions. All such modifications are intended to be within the scope of claims associated with this disclosure.

Any of the devices described for carrying out the subject diagnostic or interventional procedures may be provided in packaged combination for use in executing such interventions. These supply "kits" may further include instructions for use and be packaged in sterile trays or containers as commonly employed for such purposes.

The invention includes methods that may be performed using the subject devices. The methods may comprise the act of providing such a suitable device. Such provision may be performed by the end user. In other words, the "providing" act merely requires the end user obtain, access, approach, position, set-up, activate, power-up or otherwise act to provide the requisite device in the subject method. Methods recited herein may be carried out in any order of the recited events which is logically possible, as well as in the recited order of events.

Exemplary aspects of the invention, together with details regarding material selection and manufacture have been set forth above. As for other details of the present invention, these may be appreciated in connection with the above-referenced patents and publications as well as generally known or appreciated by those with skill in the art. For example, one with skill in the art will appreciate that one or more lubricious coatings (e.g., hydrophilic polymers such as polyvinylpyrrolidone-based compositions, fluoropolymers such as tetrafluoroethylene, hydrophilic gel or silicones) may be used in connection with various portions of the devices, such as relatively large interfacial surfaces of movably coupled parts, if desired, for example, to facilitate low friction manipulation or advancement of such objects relative to other portions of the instrumentation or nearby tissue structures. The same may hold true with respect to method-based aspects of the invention in terms of additional acts as commonly or logically employed.

In addition, though the invention has been described in reference to several examples optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range, is encompassed within the invention.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in claims associated hereto, the singular forms "a," "an," "said," and "the" include plural referents unless the specifically stated otherwise. In other words, use of the articles allow for "at least one" of the subject item in the description above as well as claims associated with this disclosure. It is further noted that such claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in claims associated with this disclosure shall allow for the inclusion of any additional element—irrespective of whether a given number of elements are enumerated in such claims, or the addition of a feature could be regarded as transforming the nature of an element set forth in such claims. Except as specifically defined herein, all technical and scientific terms used herein are to be given as broad a commonly understood meaning as possible while maintaining claim validity.

The breadth of the present invention is not to be limited to the examples provided and/or the subject specification, but rather only by the scope of claim language associated with this disclosure.

The invention claimed is:

1. A system for injecting, comprising:
a syringe body defining an interior medicine chamber;
a stopper member configured to be inserted into the interior medicine chamber to contain medicine within the medicine chamber;
a plunger member configured to be manually manipulated to insert the stopper member relative to the syringe body;
a needle having proximal and distal ends, the proximal end comprising an anchoring geometry configured to be at least partially penetrated into the stopper member;
an energy-storing member operatively coupled between the stopper member and the syringe body, the energy-storing member configured to facilitate retraction of the needle relative to the syringe body;
a needle latch having a latched position, in which the needle latch prevents proximal movement of the needle relative to the syringe body, and an unlatch position, in which the needle latch allows proximal movement of the needle relative to the syringe body; and
a needle latch actuating member configured to move the needle latch from the latched position to the unlatch position when the needle latch actuating member is moved distally relative to the needle latch in the latched position,
wherein the needle and the needle latch actuating member are configured such that moving the needle distally causes the needle to apply a distally directed force to the needle latch actuating member, causing the needle latch actuating member to move distally, thereby moving the needle latch from the latched position to the unlatched position.

2. The system of claim 1, wherein the plunger member comprises a plunger member body that defines an interior volume, and wherein the energy-storing member is housed substantially inside of the plunger member body interior volume.

3. The system of claim 2, further comprising a latch member operatively coupled to the plunger member and housed substantially within the plunger member body interior volume, the latch member being configured to have a first mechanical state wherein the latch member maintains the energy storing member in an energy-storing state, and a second mechanical state wherein the latch member allows the energy-storing member to release energy stored by the energy-storing member to assist in retraction of the needle relative to the syringe body.

4. The system of claim 3, wherein the latch member comprises triggering portion configured to extend outside of the plunger member body interior volume and operatively couple to the syringe body such that the energy-storing member may be automatically released when the plunger member and intercoupled stopper member reach a predetermined insertional position relative to the syringe body.

5. The system of claim 4, wherein the predetermined insertional position is one wherein the stopper is positioned in a full insertion state relative to the syringe body.

6. The system of claim 4, wherein the plunger member and intercoupled stopper member reach the predetermined insertional position relative to the syringe body after the needle latch actuating member has moved the needle latch from the latched position to the unlatch position.

7. The system of claim 1, wherein the energy-storing member is a spring.

8. The system of claim 7, wherein the spring comprises a material selected from the group consisting of: stainless steel, carbon steel, beryllium copper alloy, nickel-titanium alloy, chrome-silicon alloy, cobalt-nickel alloy, a styrenic polymer, a co-polyester polymer, polyurethane, polyamide, a polyolefin blend, a polyolefin alloy, a polyolefin plastomer, a polyolefin plastomer, and rubber.

9. The system of claim 7, wherein the spring comprises a generally helically-shaped coil.

10. The system of claim 1, wherein retraction of the needle comprises withdrawing at least a portion of the needle into the interior medicine chamber of the syringe body.

11. The system of claim 1, wherein the plunger member has a threaded tip, and a hollow recess.

12. The system of claim 11, wherein the hollow recess is configured to allow the needle proximal end to fully penetrate the stopper.

13. The system of claim 1, wherein the syringe body comprises glass or polymer.

14. The system of claim 1, wherein the stopper member comprises butyl rubber.

15. The system of claim 1, wherein the needle latch actuating member includes a hole configured to receive the needle distal end.

16. The system of claim 1, wherein the needle has a notch configured to engage the needle latch in the latched position to prevent proximal movement of the needle relative to the syringe body.

17. The system of claim 16, wherein moving the needle latch from the latched position disengages the needle latch from the notch to allow proximal movement of the needle relative to the syringe body.

18. The system of claim 1, wherein the needle latch comprises a flexible arm.

19. The system of claim 18, wherein the needle latch comprises a pair of flexible arms.

20. The system of claim 19, wherein moving the needle latch actuating member distally relative to the needle latch in the latched position the needle latch moves the pair of flexible arms apart from each other.

* * * * *